(12) United States Patent
Tracey et al.

(10) Patent No.: US 7,942,806 B2
(45) Date of Patent: May 17, 2011

(54) STRESS URINARY INCONTINENCE IMPLANT AND DEVICE FOR DEPLOYING SAME

(75) Inventors: Michael R. Tracey, Branchburg, NJ (US); Steve Bell, Rome (IT); Bryan Knodel, Flagstaff, AZ (US)

(73) Assignee: Ethicon, Inc., Somerville, NJ (US)

( * ) Notice: Subject to any disclaimer, the term of this patent is extended or adjusted under 35 U.S.C. 154(b) by 915 days.

(21) Appl. No.: 11/321,659

(22) Filed: Dec. 29, 2005

(65) Prior Publication Data

US 2007/0156012 A1 Jul. 5, 2007

(51) Int. Cl.
*A61F 2/00* (2006.01)
(52) U.S. Cl. .......................................................... 600/29
(58) Field of Classification Search ................ 600/37, 600/29–32; 606/119, 139, 144, 148, 151, 606/232; 128/834, 885
See application file for complete search history.

(56) References Cited

U.S. PATENT DOCUMENTS

| | | | | | |
|---|---|---|---|---|---|
| 5,755,236 | A | * | 5/1998 | Dann et al. | 128/885 |
| 5,785,640 | A | * | 7/1998 | Kresch et al. | 600/29 |
| 5,795,346 | A | * | 8/1998 | Achter et al. | 604/385.18 |
| 5,899,909 | A | | 5/1999 | Claren et al. | 606/119 |
| 6,039,686 | A | | 3/2000 | Kovac | 600/30 |
| 6,048,306 | A | * | 4/2000 | Spielberg | 600/29 |
| 6,056,687 | A | * | 5/2000 | Polyak et al. | 600/29 |
| 6,418,930 | B1 | | 7/2002 | Fowler | 128/830 |
| 6,460,542 | B1 | * | 10/2002 | James | 128/885 |
| 6,595,911 | B2 | | 7/2003 | LoVuolo | 600/30 |
| 6,599,318 | B1 | * | 7/2003 | Gabbay | 623/11.11 |

(Continued)

FOREIGN PATENT DOCUMENTS

WO WO 97/43982 11/1997

(Continued)

OTHER PUBLICATIONS

Morgan N. Medical Shape Memory Alloy Applications—the market and its products. Materials Science and Engineering A 378: 16-23, 2004.*

*Primary Examiner* — Charles A Marmor, II
*Assistant Examiner* — Catherine E. Burk

(57) ABSTRACT

A suburethral implant for treating stress urinary incontinence (SUI) includes an elongated plate-like member which is slightly curved in transverse cross-section, and a pair of spaced apart arms having hooked ends or barbs which extend from the plate-like member. A device for deploying the suburethral implant for treating SUI includes a vaginal probe for insertion in the vaginal canal of a patient, and a urethra locator probe for the simultaneous insertion in the urethra of a patient. The urethra probe is spaced apart from and overlies the vaginal probe. The vaginal probe includes a wall in which is formed an exit port. A suburethral implant introducer assembly is extendable and retractable through the exit port on the vaginal probe. The introducer assembly has a distal end on which is removably mounted a suburethral implant. The introducer assembly is extendable through the exit port to pierce the vaginal canal wall of the patient in order to position the suburethral implant in proximity to the patient's urethra. The hooked ends or barbs on the arms of the suburethral implant engage the tissue surrounding the patient's urethra and are affixed thereto during deployment of the implant. The introducer assembly is then retracted into the vaginal probe, whereby the implant is released from the introducer assembly and remains affixed to tissue in proximity to the patient's urethra.

46 Claims, 14 Drawing Sheets

U.S. PATENT DOCUMENTS

| | | | |
|---|---|---|---|
| 6,679,831 B1 * | 1/2004 | Zunker et al. | 600/29 |
| 6,808,486 B1 * | 10/2004 | O'Donnell | 600/30 |
| 6,824,560 B2 * | 11/2004 | Pelton | 623/1.15 |
| 7,070,558 B2 * | 7/2006 | Gellman et al. | 600/37 |
| 7,771,344 B2 * | 8/2010 | Ziv | 600/29 |
| 2001/0044652 A1 | 11/2001 | Moore | 623/1.16 |
| 2003/0191360 A1 * | 10/2003 | Browning | 600/29 |
| 2003/0216814 A1 | 11/2003 | Siegel et al. | 623/23.66 |
| 2004/0084054 A1 * | 5/2004 | Kaseki et al. | 128/885 |
| 2004/0143152 A1 | 7/2004 | Grocela | 600/30 |
| 2005/0250978 A1 * | 11/2005 | Kammerer | 600/29 |
| 2006/0264698 A1 * | 11/2006 | Kondonis et al. | 600/37 |

FOREIGN PATENT DOCUMENTS

| | | |
|---|---|---|
| WO | WO 0126588 A2 * | 4/2001 |
| WO | WO 2005/087154 | 9/2005 |

* cited by examiner

STRESS URINARY INCONTINENCE IMPLANT AND DEVICE FOR DEPLOYING SAME

BACKGROUND OF THE INVENTION

1. Field of the Invention

This invention relates to procedures and devices for treating stress urinary incontinence (SUI), and more particularly relates to the use of implants for treating SUI and devices for deploying such implants.

2. Description of the Prior Art

Stress urinary incontinence (SUI) is a female medical condition associated with the weakening of the pelvic muscles and/or connective tissues-which support the urethra in its proper position. As a result of this condition, involuntary urine leakage occurs from simple physical activity, such as running or jumping, and even coughing or sneezing, as the urethra is not properly supported and does not remain fully closed during such activity.

A widely accepted medical procedure to correct SUI is the insertion of a trans-vaginal tape (TVT). The TVT is an elongated polypropylene mesh tape which is surgically implanted in the pelvic tissue to partially surround and provide support for the urethra. A conventional TVT is disclosed in U.S. Pat. No. 5,899,909, which issued to Jan Claren et al.

The conventional procedure for treating SUI using a TVT is to surgically insert one end of the mesh tape through an incision in the vaginal wall on one lateral side of the urethra using an elongated curved needle, through the pelvic tissue behind the pubic bone, and exiting through an incision made in the abdominal wall. The procedure is repeated for the other end of the mesh tape, this time on the other lateral side of the urethra, with the needle exiting through a second incision made in the abdominal wall of the patient. After the mesh tape is tightened for proper support of the urethra, its free ends extending outside of the abdominal wall are trimmed.

One of the disadvantages of trans-vaginal tapes is that they require two separate, albeit minimal, incisions made through the abdominal wall through which exit the curved needles to which the mesh tape ends attach. Although this involves a minimally invasive surgical procedure, it is still considered major surgery by patients. Also, the external incisions increase the risk of postoperative infection to at least a small degree.

Trans-vaginal slings are also conventionally used for treating SUI. Current slings require abdominal incisions and use anchors, e.g., staples, to implant the sling. Furthermore, conventional trans-vaginal slings further require anchoring the sling to the patient's pubic bone and/or abdomen, thus requiring multiple incisions, stitching and the like throughout the patient's pelvic region. This surgical procedure often requires general or spinal anesthesia to be administered to the patient. Additionally, there is usually a prolonged recovery associated with this procedure, with a concomitant reduction in the patient's ambulatory functions. A vaginal sling, for example, is disclosed in U.S. Pat. No. 6,039,686, which issued to S. Robert Kovac.

OBJECTS AND SUMMARY OF THE INVENTION

It is an object of the present invention to provide an implant for the treatment of stress urinary incontinence (SUI) which requires no incisions in the abdominal wall.

It is another object of the present invention to provide an implant for treating SUI which requires no needles for its surgical placement in a patient.

It is still another object of the present invention to provide an implant for treating SUI which facilitates and shortens the surgical procedure for deploying the implant in the patient.

It is a further object of the present invention to provide a less invasive SUI therapy for patients having less severe symptoms.

It is yet a further object of the present invention to provide an implant for treating SUI which appears less invasive and frightening to the patient by not requiring elongated needles conventionally used with trans-vaginal tapes.

It is still a further object of the present invention to provide an implant for treating SUI which requires less anesthesia during the surgical procedure to deploy the implant.

It is still another object of the present invention to provide a device for deploying an implant for the treatment of SUI.

It is a further object of the present invention to provide a method for treating SUI by using a suburethral implant formed in accordance with the present invention.

It is yet a further object of the present invention to provide a minimally invasive surgical procedure for deploying an implant for treating SUI.

It is still a further object of the present invention to provide an implant for treating SUI which overcomes the disadvantages of conventionally used implants, such as trans-vaginal tapes.

In accordance with one form of the present invention, a suburethral implant for treating stress urinary incontinence (SUI) has a general shape that includes two arms supporting a middle section. The arms have barbs or hooks on their ends that catch on the tissue when the implant is deployed. The implant, when deployed, straddles the urethra, with the middle section providing lift for the urethra.

In another form of the present invention, a device for deploying the suburethral implant includes a vaginal probe which is inserted into the vaginal canal of a patient. The device also includes a urethra locator probe which is inserted into the patient's urethra in order to hold steady at least a portion of the patient's urethra in a particular position with respect to the vaginal probe. The vaginal probe has an opening formed through the thickness of the probe's wall.

The device further includes a suburethral implant introducer assembly which is extendable and retractable with respect to the vaginal probe through the opening formed in the vaginal probe. The introducer assembly has a distal end on which is removably mounted a suburethral implant, such as described previously.

The urethra locator probe is received by a patient's urethra for positioning the urethra in a desired location with respect to the vaginal probe. The introducer assembly is extendable with respect to the vaginal probe to pierce the vaginal canal wall of the patient so as to position the suburethral implant that is removably mounted on the end of the introducer assembly in proximity to the patient's urethra. The introducer assembly is then retracted through the opening in the vaginal probe. The barbs or hooks on the ends of the implant arms catch on the tissue and remain affixed thereto as the introducer assembly is retracted. The implant straddles and provides lift to the urethra.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Figure 1:
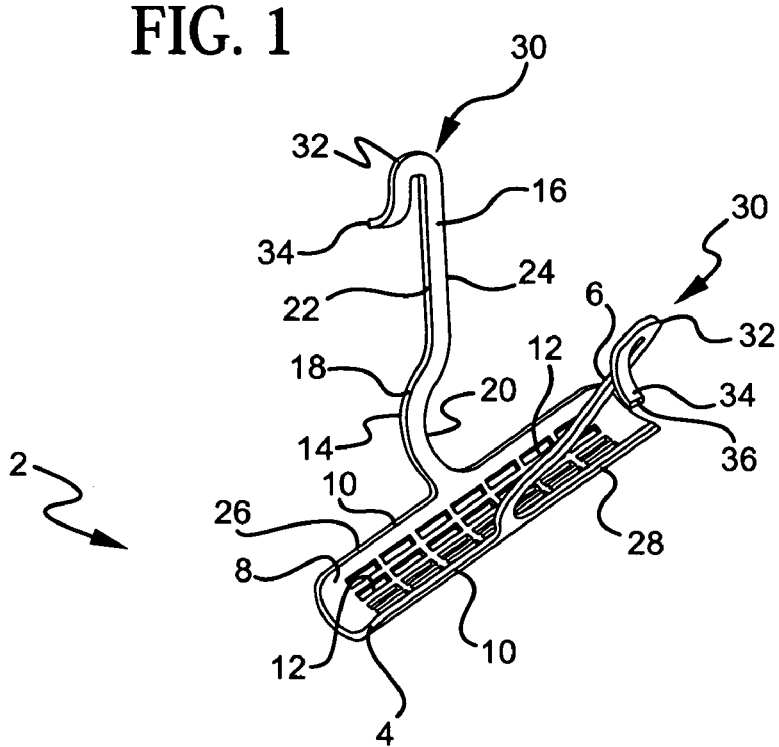
FIG. 1 is a perspective view of an implant for treating stress urinary incontinence (SUI) formed in accordance with one form of the present invention.

In accordance with one form of the present invention, it will be seen that an implant 2 for treating stress urinary incontinence (SUI), which implant 2 is also referred to as a suburethral implant, as it is preferably positioned beneath a patient's urethra to lift and support the urethra in order to overcome the symptoms associated with SUI, includes a main body 4 for supporting a patient's urethra, and a pair of spaced apart arms 6. The main body 4 of the suburethral implant includes an elongated, plate-like middle section or member 8 having a longitudinal axis along which the plate-like member 8 extends, and opposite lateral side portions 10. The pair of spaced apart arms 6 extend from the plate-like member 8 preferably from the opposite lateral side portions 10 thereof and generally in an upward or transverse direction from the plate-like member.

Figure 2:
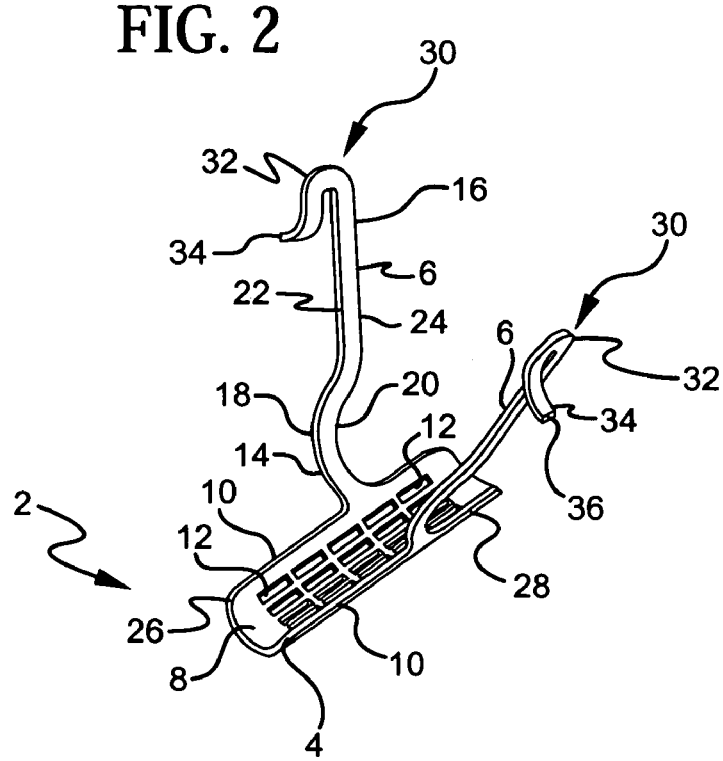
FIG. 2 is a perspective view of an implant for treating SUI formed in accordance with a second form of the present invention.
Figure 2A:
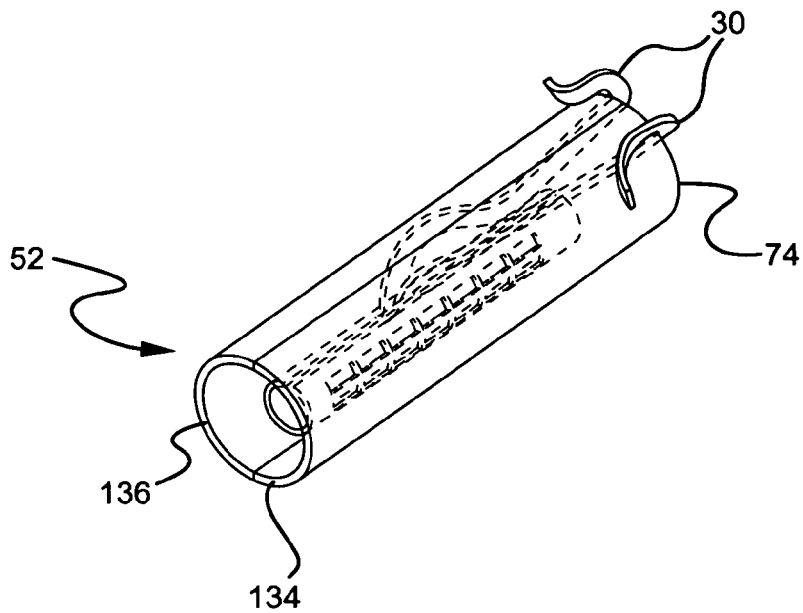
FIG. 2A is a perspective view of the implant of the present invention shown in FIG. 1 folded in an undeployed state.
Figure 2B:
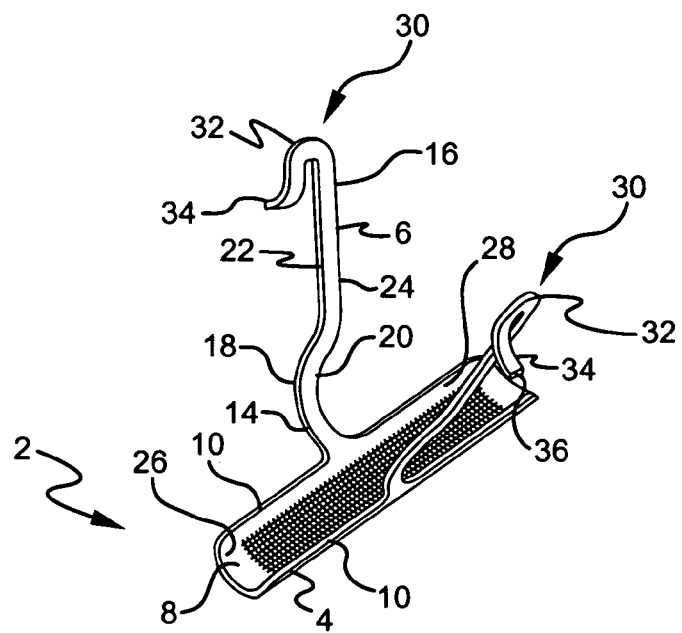
FIG. 2B is a perspective view of a third form of the implant of the present invention.

Preferably, the plate-like member 8 of the main body 4 is concave in transverse cross-section to cradle and support a patient's urethra or the tissue surrounding the urethra. The plate-like member 8 also preferably includes a plurality of openings 12 formed through its thickness to allow the flow of fluids into the tissue supported thereby. Even more preferably, the plate-like member 8 of the main body 4 is at least partially formed from a mesh material, such as shown in FIG. 2B.

Each arm 6 extends outwardly and upwardly from the opposite lateral side portions 10 of the plate-like member 8 of the main body 4, and includes a proximate end 14 which attaches to the main body of the implant, and a distal, free end 16 opposite the proximate end 14. As further will be described in greater detail, each arm 6 preferably includes a spring portion 18 which may be in the form of a curved section of the arm 6 situated near the proximate end 14. The curved portion 18 of each arm defines an open pocket 20 for at least partially receiving a portion of the plate-like member 8 of the main body 4 so that the plate-like member and/or the arms may be folded to extend along the same longitudinal axis as the plate-like member in an undeployed state.

Stated another way, each arm 6 includes a first side 22 and a second side 24 opposite the first side 22, and the plate-like member 8 includes a first portion 26 extending outwardly from the first side 22 of the arms in a first direction along the longitudinal axis of the plate-like member 8, and a second portion 28 extending outwardly from the second side 24 of the arms in a second direction along the longitudinal axis of the plate-like member 8 which is opposite to the first direction. The suburethral implant 2 is foldable in a first undeployed state, such as shown in FIG. 2A wherein the second portion 28 is at least partially received by the open pockets 20 defined by the curved sections 18 of the arms 6 such that the arms and second portion 28 of the plate-like member 8 extend generally in the second direction along the longitudinal axis of the plate-like member 8. The suburethral implant 2 may be unfolded to a second deployed state, wherein the second portions 28 of the plate-like member 8 pivot out of the open pockets 20 defined by the curved sections 18 of the arms such that the arms 6 extend in a transverse direction to the longitudinal axis in which the first and second portions 26, 28 of the plate-like member extend, such as shown in FIG. 1 of the drawings.

The suburethral implant of the present invention, and more specifically, either or both of the plate-like member 8 of the main body 4 and the pair of spaced apart arms 6, is preferably formed from either a resilient, elastically deformable material, such as certain polymers and elastomers which are well known to those skilled in the art, or a deformable material having shape memory properties, such as the alloy Nitinol. The arms 6 and/or the member 8 may also be formed from polypropylene or the like to form a permanent, non-absorbable implant, or from an absorbable material, such as a molded vicryl. Formed of such materials, the suburethral implant 2 of the present invention is deformable between the undeployed state, as mentioned previously, where the arms 6 are folded down to meet the plate-like member 8 of the main body 4 and where both extend generally along the same longitudinal axis, as shown in FIG. 2A, and in its deployed state to support a patient's urethra, where the spaced apart arms 6 extend transversely to the longitudinal axis of the plate-like member 8, such as shown in FIG. 1 of the drawings. The preferably curved, plate-like member 8 may also be rolled into a small diameter tube in the undeployed state, as shown in FIG. 2A, so that the plate-like member 8 and arms 6 may be held within a suburethral implant introducer assembly 52, which is a component in a device of the present invention that may be used for deploying the implant in a patient's body. When released by the introducer assembly of the deployment device, the plate-like member 8 will unroll and the arms 6 will spring out transversely from the plate-like member due to their elasticity, to a deployed form straddling and supporting the patient's urethra.

Figure 3:
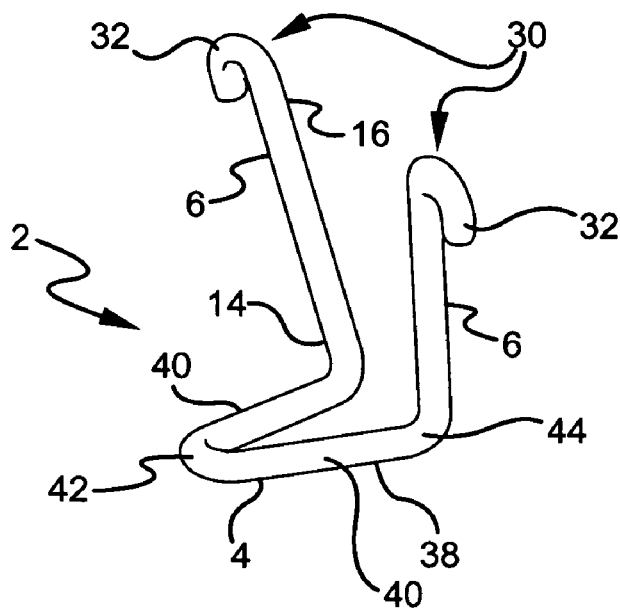
FIG. 3 is a perspective view of an implant used for treating SUI formed in accordance with a fourth form of the present invention.

Each arm 6 of the implant 2 preferably includes a tissue engaging portion 30 that is preferably situated at the distal free end 16 of the arm. More specifically, the tissue engaging free end of each arm 6 may include a hooked end 32, such as shown in FIG. 3 of the drawings, and/or a barb 34, which may be defined by a portion of the free end 16 of the arm turned to extend outwardly from the plane in which each arm preferably resides, the barb 34 of one arm 6 facing in an opposite direction to that of the barb 34 of the other arm, such as shown in FIG. 1 of the drawings. The hooked ends 32 and the barbs 34 of the spaced apart arms 6 engage the tissue surrounding the urethra when implanted in a patient to facilitate securing the suburethral implant to tissue in proximity to the patient's urethra. Preferably, the hooked ends 32 or barbs 34 of the arms 6 engage tissue on opposite sides of the urethra, with the plate-like member 8 of the main body 4 situated therebetween and cradling a portion of the urethra or tissue surrounding the urethra. Each barb 34 may have a sharpened tip or portion 36 which further ensures that the arm 6 will pierce and penetrate the tissue at the desired location to securely anchor the arms and the implant 2 in place in proximity to and supporting the patient's urethra.

Of course, it should be understood that the arms 6 may include barbs and hooks along portions thereof other than at their distal free ends 16 in order to anchor the implant in place, and such embodiments are envisioned to be within the scope of the present invention.

The plate-like member 8 of the main body 4 of the suburethral implant 2 may be made with different longitudinal lengths. For example, FIG. 1 illustrates a "long body" version of the suburethral implant 2 of the present invention. Here, the plate-like member 8 has a longitudinal length between about 0.5 mm and about 10 mm, and more preferably has a longitudinal length of about 3 mm. A "short body" version of the suburethral implant 2 of the present invention is shown in FIG. 2. In this particular embodiment, the plate-like member 8 of the main body 4 preferably has a longitudinal length of about 2 mm.

A surgeon may prefer one length for the implant over the other for different reasons, including the patient's age and the physiological makeup of the patient's body. The "short body" version may be more easily deployed and appropriately positioned, but the "long body" version may be preferred, as it creates less concentrated load on the patient's urethra.

Preferably, for the embodiment of the suburethral implant 2 shown in FIGS. 1 and 2, the length of each arm 6 is between about 1 mm and about 10 mm, and more preferably is about 2 mm.

Another form of the suburethral implant 2 of the present invention is shown in FIG. 3 of the drawings. Here, the implant includes a main body 4, as in the prior embodiment, for supporting a patient's urethra, and a pair of spaced apart arms 6 extending from the main body 4. However, the main body 4 preferably is formed from a V-shaped member 38 extending along a longitudinal plane and having a pair of legs 40 connected together at a flexible apex joint 42, and the pair of spaced apart arms 6 extend from the V-shaped member 38 and are connected to the ends of the legs 40 also at flexible joints 44. As in the previous embodiment shown in FIGS. 1 and 2 of the drawings, each arm 6 preferably has a tissue engaging portion 30 preferably situated at its free end 16.

Whereas the embodiment of the suburethral implant shown in FIGS. 1 and 2 may be cut from a tubular piece of Nitinol, the suburethral implant of the present invention shown in FIG. 3 may be constructed such that the V-shaped member 38 and each arm 6 are integrally formed from a single, selectively shaped, rod-like member, such as Nitinol wire. As mentioned above, the arms 6 and the legs 40 of the V-shaped member 38 are preferably joined at flexible joints 42, 44 so that the arms may be bent downwardly to reside in substantially the same plane as the V-shaped member, and the legs 40 may be folded together so that the suburethral implant 2 may be compactly received within the suburethral implant introducer assembly 52 of a device for deploying the implant, as will be described further in greater detail. Furthermore, the V-shaped member 38 and/or each arm 6 may be formed from either a resilient, elastically deformable material, as in the embodiment shown in FIGS. 1 and 2, or a material having shape memory properties, such as Nitinol.

Figure 3A:
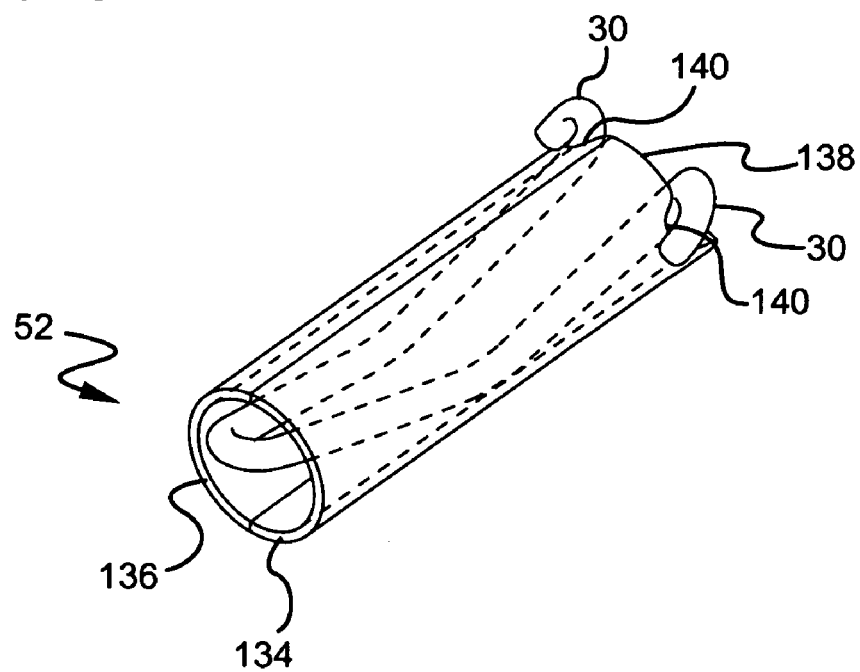
FIG. 3A is a perspective view of the implant of the present invention shown in FIG. 3 folded in an undeployed state.

More specifically, the suburethral implant 2 of the present invention shown in FIG. 3 is foldable to an undeployed state in which the arms 6 and the V-shaped member 38 extend generally along the longitudinal plane of the V-shaped member, as shown in FIG. 3A, and the suburethral implant 2 is unfoldable to a deployed state in which the arms 6 extend in a transverse direction to the longitudinal plane in which the V-shaped member 38 resides and the legs 40 of the V-shaped member are angled outwardly from one another, as shown in FIG. 3.

In a similar manner to the embodiment shown in FIGS. 1 and 2, the suburethral implant 2 shown in FIG. 3 preferably includes a tissue engaging portion 30 at the distal end 16 of each arm 6. The tissue engaging free end may include a barb 34 or hook 32 to facilitate securing the suburethral implant to tissue in proximity to the patient's urethra.

The wire-constructed implant 2 of the present invention shown in FIG. 3 has certain advantages, including the fact that it occupies very little space when in its undeployed shape and, accordingly, may be more easily deployed with little or no trauma to a patient by a device used to position and selectively release the implant at a position to cradle the patient's urethra. The urethra would be received between the upstanding arms 6 and cradled by the V-shaped member 38, with the hooked ends 32 of the arms securing the suburethral implant in place to the tissue surrounding the urethra.

For the embodiment shown in FIG. 3, the suburethral implant 2 of the present invention has each arm 6 dimensioned to have a length of between about 1 mm and about 10 mm, and more preferably has a length of about 2 mm. The V-shaped member 38, from its flexible apex joint 42 to its arm joints 44, preferably has a longitudinal length of between about 1 mm and about 10 mm, and a more preferred length of about 2 mm.

Figure 4:
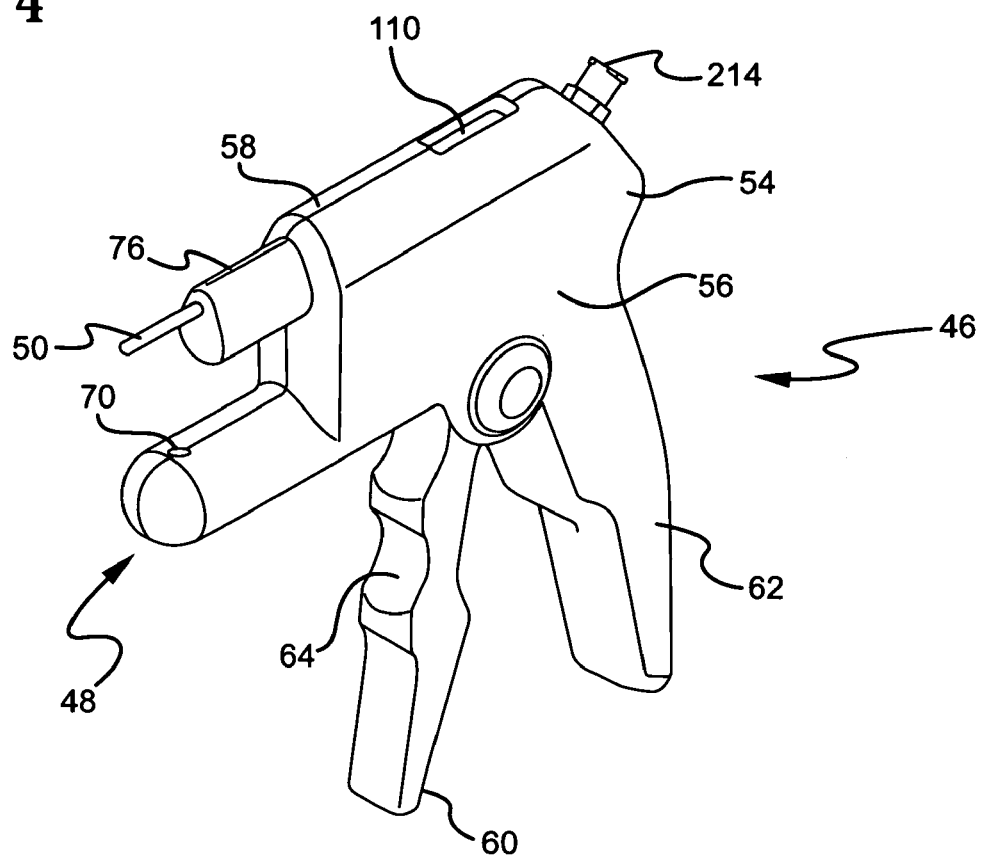
FIG. 4 is a front perspective view of a device formed in accordance with the present invention for deploying an implant, such as those shown in FIGS. 1-3, for treating SUI.
Figure 5:
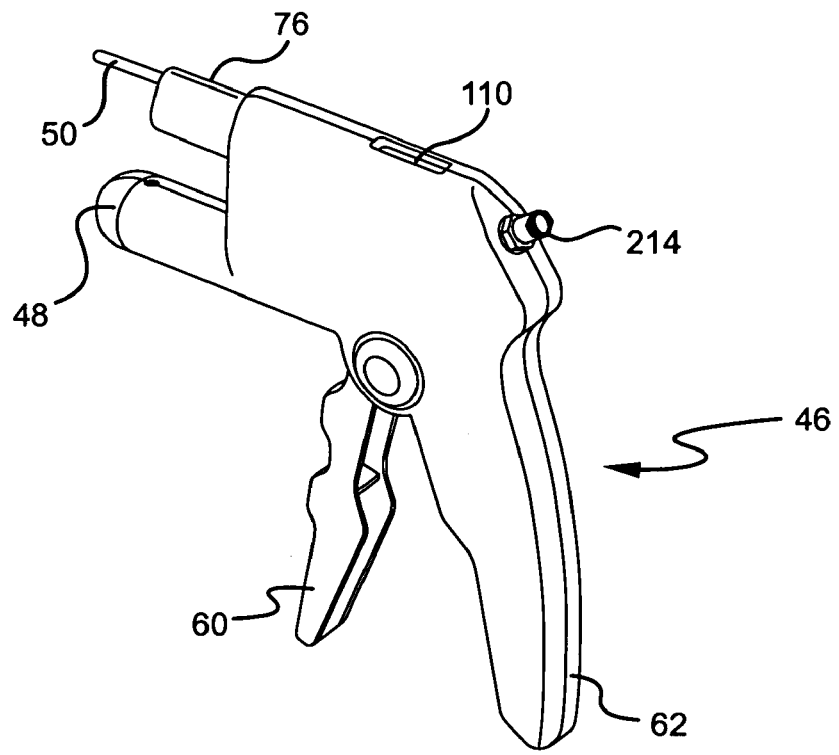
FIG. 5 is a rear perspective view of the device of the present invention shown in FIG. 4.
Figure 6:
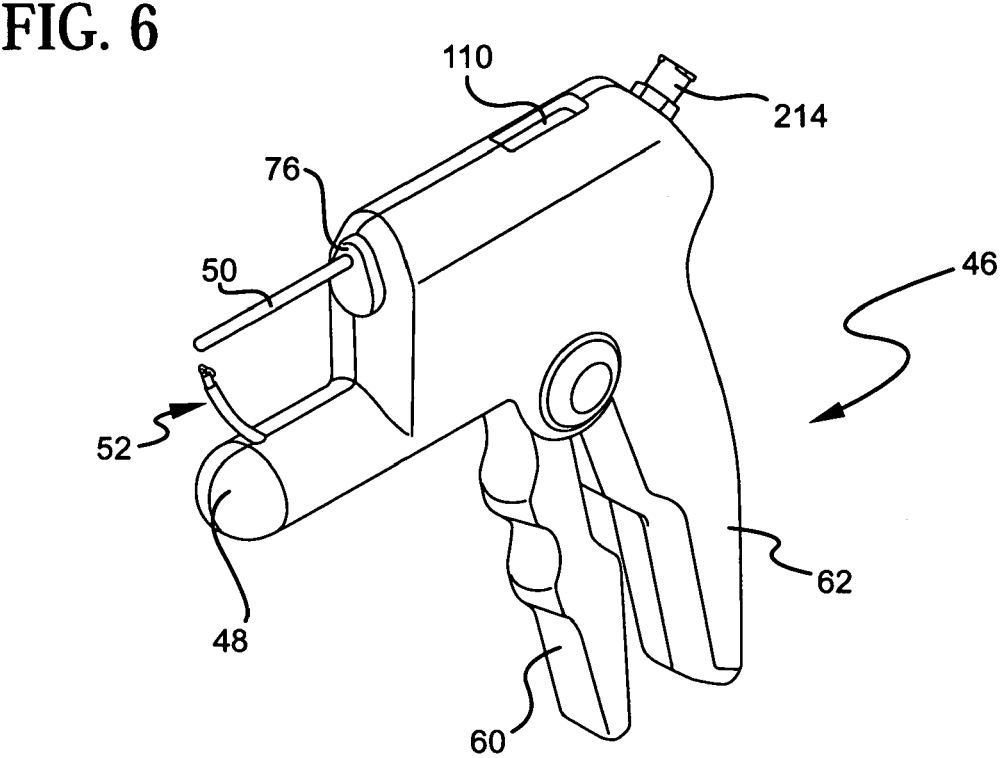
FIG. 6 is a front perspective view of the device of the present invention shown in FIGS. 4 and 5 and illustrating the operation of the device.
Figure 7:
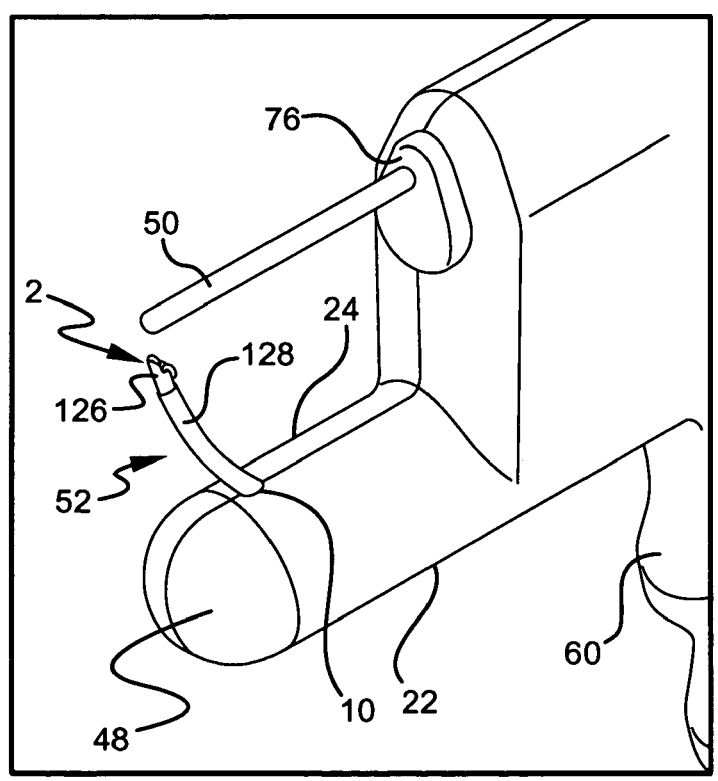
FIG. 7 is an enlarged, front perspective view of a portion of the device of the present invention shown in FIGS. 4 and 5 and illustrating the operation of the device in deploying an implant for treating SUI.
Figure 8:
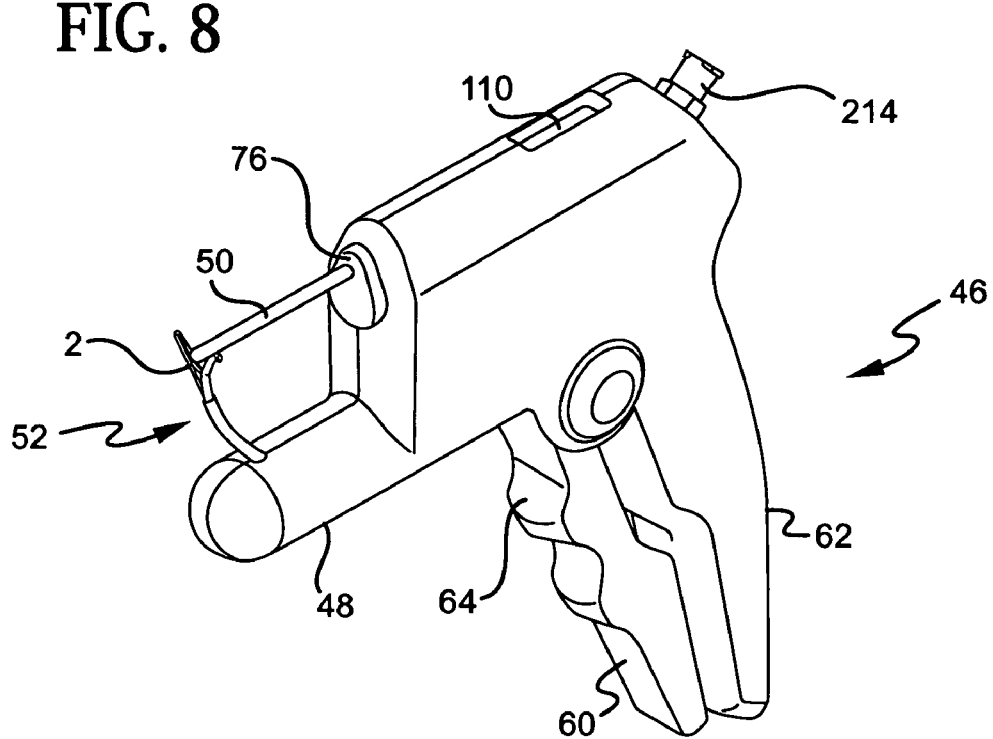
FIG. 8 is a front perspective view of the device of the present invention shown in FIGS. 4 and 5 and illustrating the operation of the device in deploying an implant for treating SUI.
Figure 9:
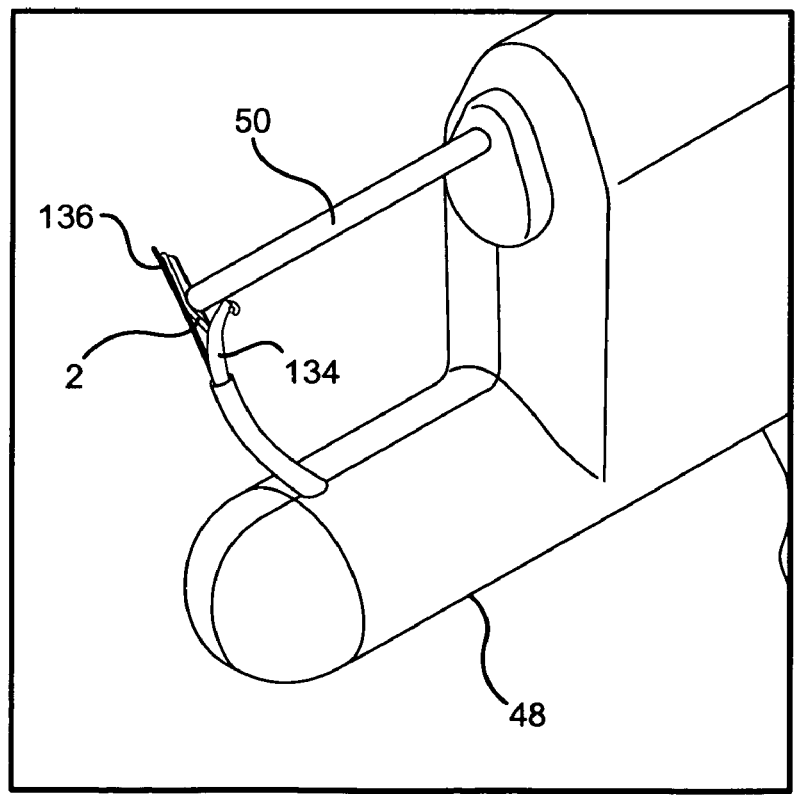
FIG. 9 is an enlarged front perspective view of a portion of the device of the present invention shown in FIGS. 4 and 5 and illustrating the operation of the device in deploying an implant for treating SUI.
Figure 10:
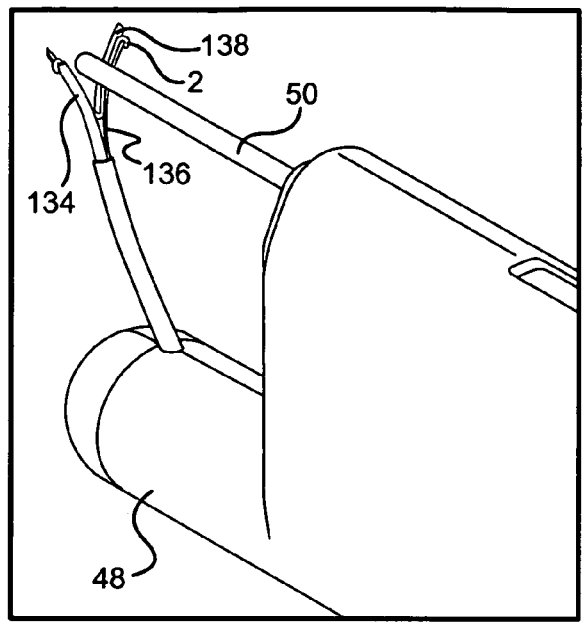
FIG. 10 is an enlarged rear perspective view of a portion of the device of the present invention shown in FIGS. 4 and 5 and illustrating the operation of the device in deploying an implant for treating SUI.
Figure 11:
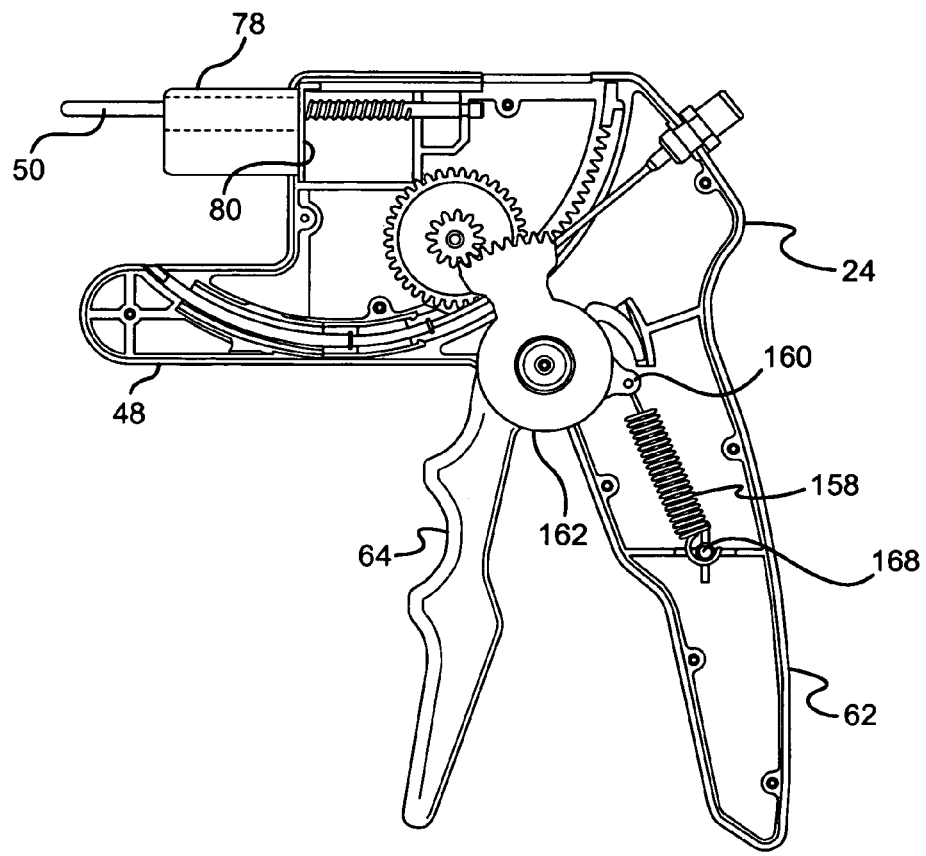
FIG. 11 is a partial cross-sectional view of the device of the present invention shown in FIGS. 4 and 5.

FIGS. 4-22 illustrate a device 46 for deploying a suburethral implant, such as those shown in FIGS. 1-3, for treating a patient suffering from stress urinary incontinence (SUI). More specifically, and referring initially to FIGS. 4 and 5 of the drawings, it will be seen that such a device 46 for deploying a suburethral implant for treating SUI constructed in accordance with the present invention includes a vaginal probe 48, a urethra locator probe 50 and a suburethral implant introducer assembly 52. More specifically, the device of the present invention includes a housing 54 which may be formed from mating first and second sections 56, 58 and on which is pivotally mounted a trigger arm 60. The housing 54 includes a handle 62 for grasping by a surgeon, and the trigger arm 60, having a finger grip portion 64, is situated pivotally in front of the handle 62. The vaginal probe 48 extends outwardly from the front wall 66 of the housing 54 as a bulbous, tubular member, with a non-traumatizing rounded distal free end 68. The vaginal probe 48 is dimensioned for insertion in the vaginal canal of a patient. The vaginal probe 48 which preferably is integrally formed from the housing wall, has a suburethral implant introducer assembly exit port 70 formed through the thickness thereof and positioned on the upper surface of the vaginal probe 48, preferably near the distal free end portion 68 of the probe.

The urethra locator probe 50 also extends outwardly from the front wall 66 of the housing 54 in a parallel direction to that of the vaginal probe 48. Preferably, the urethra locator probe 50 extends from the front wall 66 of the housing the same distance that the vaginal probe 48 extends. The urethra locator probe 50 is spaced apart from and situated to overlie the vaginal probe 48. Whereas the vaginal probe 48 is formed as a hollow tubular member, the urethra locator probe 50 is preferably formed from a solid, non-flexible rod made of stainless steel or other rigid material. The urethra locator probe 50 includes a non-traumatizing, distal free end formed with a rounded or blunt tip 72 so as not to injure or pierce the urethra when the probe is inserted therein.

As mentioned previously, the device of the present invention includes a suburethral implant introducer assembly 52, which will be further described in greater detail. The suburethral implant introducer assembly 52 is extendable and retractable with respect to the vaginal probe 48 through the introducer assembly exit port 70, i.e., the opening formed in the vaginal probe wall. The trigger arm 60 is pivotally joined to and moveable with respect to the housing 54 and is operatively coupled to the introducer assembly 52 so that the introducer assembly is extendable and retractable with respect to the vaginal probe 48 in response to pivotal movement of the trigger arm 60. The introducer assembly 52 has a distal end 74 on which is removably mounted a suburethral implant, such as the implants 2 of the present invention shown in FIGS. 1-3 of the drawings.

The urethra locator probe 50 is receivable by a patient's urethra for positioning the urethra, or at least a portion thereof, in a desired location with respect to the vaginal probe 48. The vaginal probe 48 is simultaneously inserted into the vaginal canal of the patient. Thus, a portion of the patient's vaginal canal is secured by the vaginal probe 48 in a first position, and a portion of the patient's urethra is secured by the urethra locator probe 50 in a second position relative to the first position of the portion of the patient's vaginal canal. The introducer assembly 52 is then extended with respect to the vaginal probe 48 to pierce the vaginal canal wall of the patient and to position a suburethral implant 2 that is removably mounted thereon in proximity to the patient's urethra. The introducer assembly 52 is then retracted with respect to the vaginal probe 48 through the introducer assembly exit port 70 formed in the vaginal probe, whereby the suburethral implant 2 is exposed to and engages the tissues in proximity to the patient's urethra such that the suburethral implant 2 is dislodged from the introducer assembly 52 and remains affixed to the tissue in proximity to and supporting the patient's urethra.

The operation and more preferred structure of the device 46 of the present invention for deploying an implant, such as the suburethral implants 2 shown in FIGS. 1-3, will now be described in greater detail, and reference should be had to FIGS. 4-22 of the drawings.

Preferably, the implant deployment device 46 of the present invention includes an insertion depth stop 76. The insertion depth stop 76 is mounted on the housing 54 and is engageable with the patient's body near the urethra orifice to prevent over-insertion of either or both of the urethra locator probe 50 and the vaginal probe 48 into respectively the patient's urethra and the vaginal canal. More specifically, and as shown in the partial cross-sectional views of FIGS. 11-14, the insertion depth stop 76 preferably includes a generally cylindrical plunger 78 having a bore 80 formed axially longitudinally therethrough through which is received the rod-shaped urethra locator probe 50. Even more specifically, the plunger 78 is oblong or tear-shaped in transverse cross-section, with the axial bore 80 formed therein being situated closer to the narrower side of the plunger 78, as clearly evident from FIG. 17 of the drawings. A first axial end 82 of the plunger 78 includes a radially outwardly extending flange 84, and a second axial end 86 of the plunger which is opposite to the first end 82 includes an end wall 88 which is engageable with a patient's body near the urethra orifice to prevent over-insertion of the urethra locator probe 50 and/or the vaginal probe 48 into the patient's urethra and vaginal canal. The housing 54 includes an opening 90 formed through the thickness thereof having a diameter which is slightly greater than that of the plunger 78, but less than that of the radially extending flange 84, and a shape which conforms to the transverse cross-sectional shape of the plunger 78. During assembly of the device, the plunger 78 is received by the housing opening 90 and held captive therein by the larger diameter flange 84. The plunger 78 reciprocatingly slides on the rod-like urethra locator probe 50 axially along a portion of its length. A first internal wall 92 formed within the cavity of the housing, which is spaced apart from the interior surface of the top wall 94 of the housing a distance which equals or slightly exceeds the diameter of the radially extending plunger flange 84 assures that the plunger 78 moves smoothly on the housing in a reciprocating manner, without binding or becoming skewed.

The depth stop plunger 78 is biased outwardly from the housing 54 by a compression spring 96 which is coiled about a portion of the rod-like urethra locator probe 50. One axial end 98 of the spring 96 engages a surface of the plunger 78, while the opposite axial end 100 of the spring 96 engages a second internal wall 102 of the housing. As can be seen from FIGS. 11-13 of the drawings, the rod-like urethra locator probe 50 has a reduced diameter end portion 104 which is captively received by an opening formed through the thickness of a third interior wall 106 in the housing cavity.

Alternatively, the plunger 78 may preferably be hollow to define an enlarged area for receiving the compression spring 96, and have an opening 108 formed through the thickness of the front wall of the plunger, with one axial end 98 of the compression spring 96 engaging the inside surface of the front wall of the plunger 78, thereby exerting pressure on the plunger and biasing the plunger outwardly from the front wall 66 of the housing.

Figure 12:
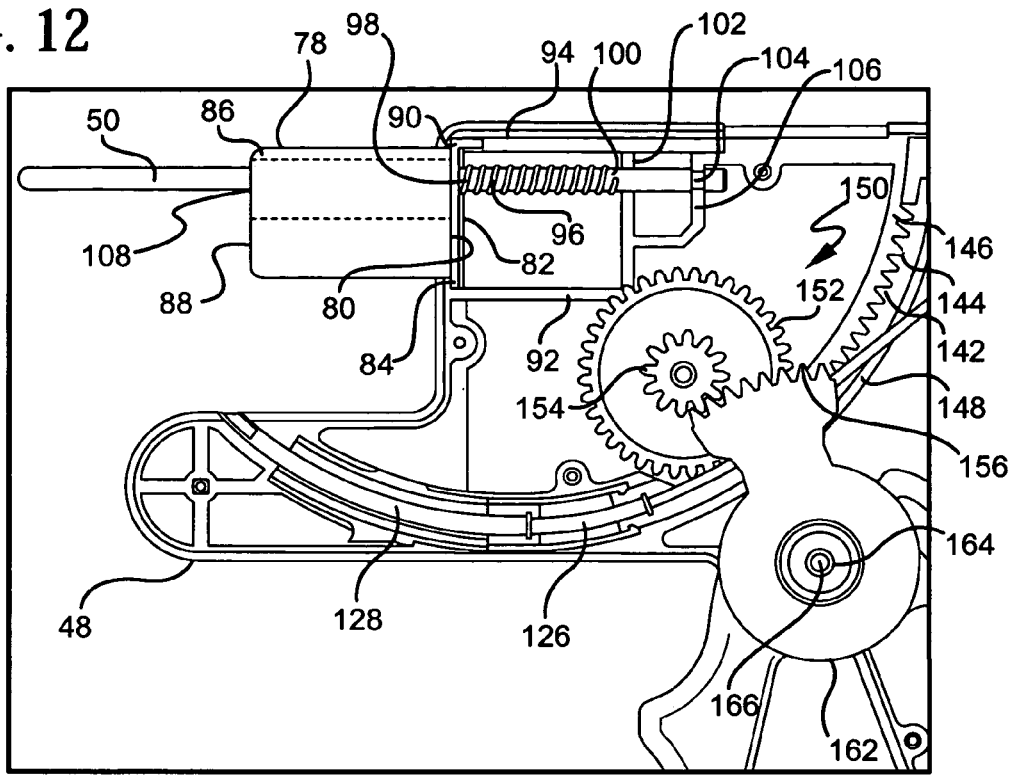
FIG. 12 is an enlarged cross-sectional view of a portion of the device of the present invention shown in FIGS. 4 and 5 for deploying an implant for treating SUI.
Figure 13:
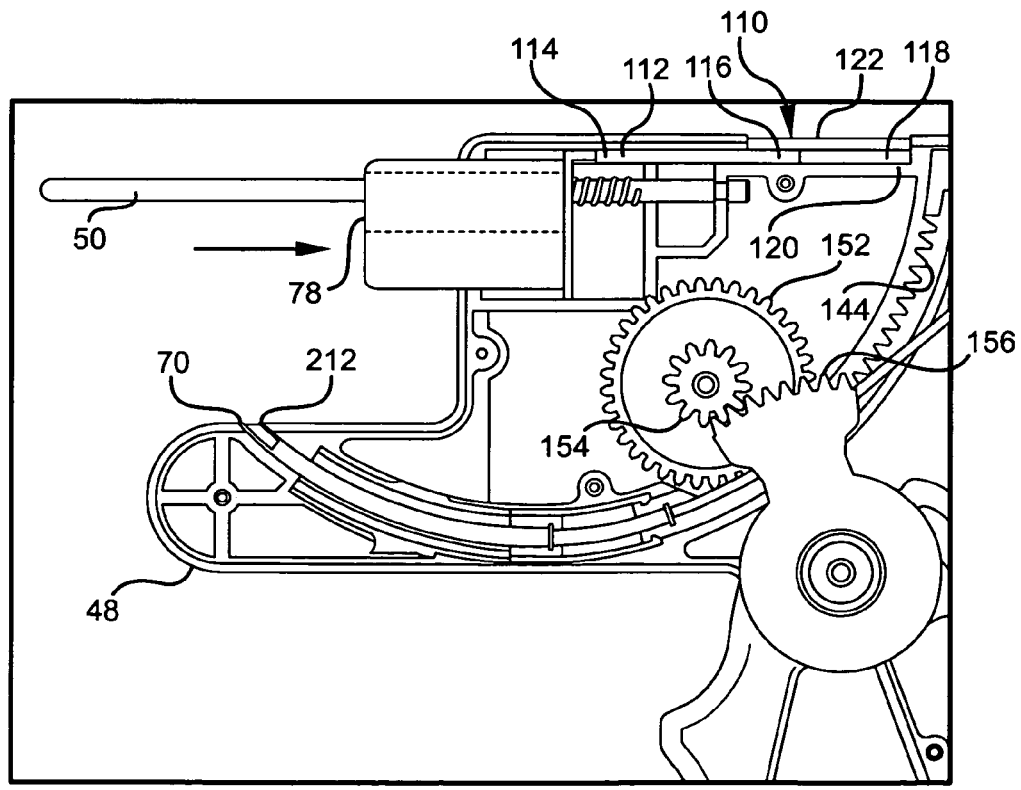
FIG. 13 is an enlarged cross-sectional view of the device of the present invention shown in FIGS. 4 and 5 and illustrating the operation of the device in deploying an implant for treating SUI.
Figure 14:
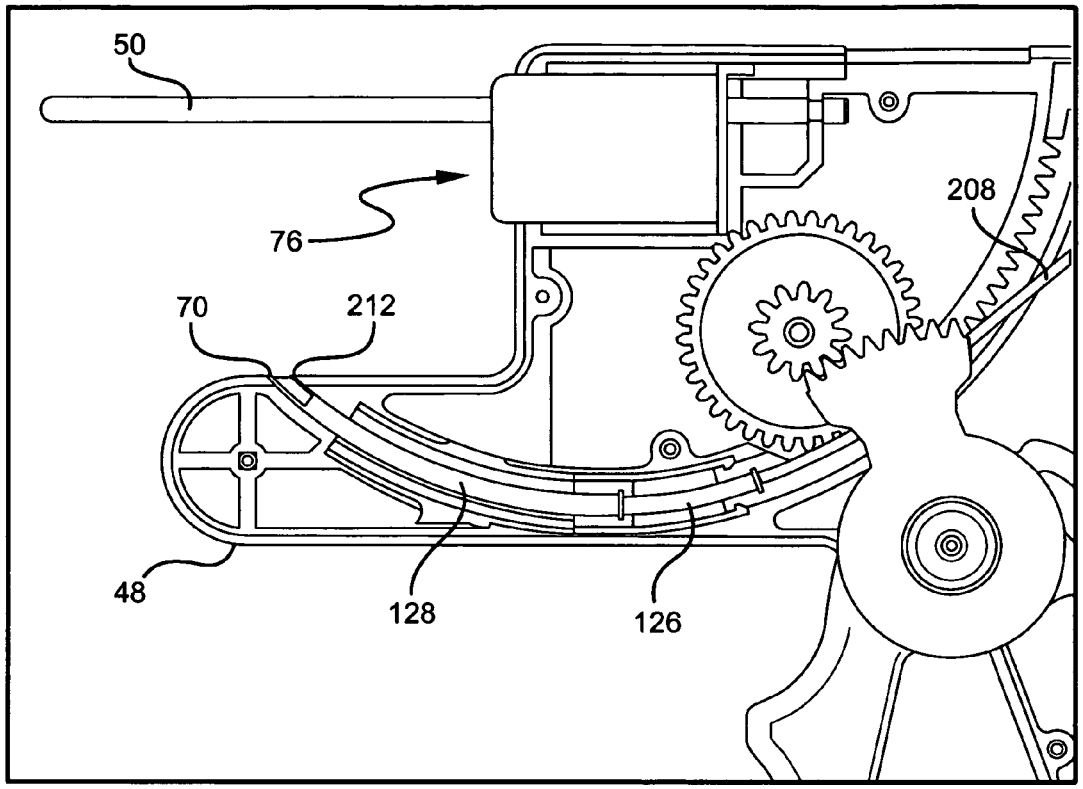
FIG. 14 is an enlarged cross-sectional view of a portion of the device of the present invention shown in FIGS. 4 and 5 and illustrating the operation of the device in deploying an implant for treating SUI.

The depth stop 76 of the implant deployment device 46 functions in the following manner. The vaginal probe 48 and the urethra locator probe 50 are simultaneously respectively inserted into the patient's vaginal canal and urethra. The front face of the plunger 78 of the depth stop 76 engages the patient's body near the urethra orifice. As the vaginal probe 48 and urethra locator probe 50 are inserted farther respectively into the patient's vaginal canal and the urethra, the plunger 78 is forced into the housing cavity against the pressure of the spring 96. The physician may decide to stop further insertion of the vaginal probe 48 and urethra locator probe 50 prior to the plunger 78 reaching the end of its stroke, and the distance to which the vaginal probe and/or locator probe are inserted respectively into the patient's vaginal canal and urethra is indicated for viewing through an insertion depth window 122 formed in the housing 54, as will be further described in greater detail. However, should the surgeon inadvertently attempt to insert the vaginal probe 48 and/or urethra locator probe 50 farther than is recommended, the first axial end of the plunger 82 engages the second internal wall 102 of the housing to prevent further movement of the plunger 78 into the housing, as shown in FIG. 14 of the drawings. Since the front wall of the plunger 78 engages the patient's body at the urethra orifice, further insertion of the vaginal probe 48 and/or the urethra locator probe 50 respectively in the vaginal canal and the urethra is prevented. When the vaginal probe 48 and urethra locator probe 50 are removed from the vaginal canal and urethra, respectively, the compressed spring 96 will force the plunger 78 back outwardly through the housing opening 90 along the length of a portion of the urethra locator probe 50 until the radially extending flange 84 on the plunger engages the inside surface of the front wall 66 of the housing, as shown in FIG. 12 of the drawings.

The device of the present invention for deploying a suburethral implant further preferably includes an insertion depth indicator 110. The insertion depth indicator 110 is responsive to movement of the plunger 78 and indicates the relative depth of insertion of either or both of the urethra locator probe 50 and the vaginal probe 48 into respectively the patient's urethra and vaginal canal. More specifically, the insertion depth indicator 110 includes an elongated plate-like member 112 having opposite first and second longitudinal axial ends 114, 116. The first end 114 of the plate-like member 112 is operatively linked, or more specifically, joined to the plunger 78 at the plunger's first axial end 114 and is reciprocatingly slidable within a narrow channel 118 defined by the inside surface of the top wall 94 of the housing and a fourth internal wall 120 spaced from the housing top wall 94. The top wall 94 of the housing includes an indicator window 122 which is preferably defined by an opening formed through the thickness of the housing top wall 94 and which is in alignment with the channel 118 in which the plate-like elongated member 112 reciprocatingly slides. At least the second axial end 116 of the elongated member 112 is aligned with the indicator window opening and is viewable by a surgeon therethrough to indicate the extend of insertion of the vaginal probe 48 and/or the urethra locator probe 50 respectively into the patient's vaginal canal and the urethra and the relative depth of the desired deployment of the suburethral implant 2 in a patient's body. An exposed surface of the plate-like elongated member 112 of the insertion depth indicator 110 may include a plurality of markings or gradations 124 which are viewable through the indicator window 122 so that the surgeon may actually measure, or relatively determine, the depth of insertion of the vaginal probe 48 and/or the urethra locator probe 50 for more precisely determining the correct position for deploying the suburethral implant 2 of the present invention in proximity to the patient's urethra.

As mentioned previously, the implant deployment device 46 of the present invention includes a suburethral implant introducer assembly 52 which is extendable and retractable through the vaginal probe exit port 70 for positioning a suburethral implant 2 that is removably mounted to the distal end 74 thereof in proximity to a patient's urethra. More specifically, the suburethral implant introducer assembly 52 includes an inner introducer feeder 126, and an outer introducer sheath 128 surrounding and selectively covering the inner introducer feeder 126. The introducer feeder 126 has a distal end 130 remotely situated from the housing when the introducer assembly 52 is in its extended state, and the suburethral implant 2 is removably mounted on the distal end 130 of the introducer feeder 126.

Even more particularly, the introducer feeder 126 includes an inner tubular member 132 having a split free end that is formed with a first portion 134 and a second portion 136 transversely adjacent to the first portion 134. The introducer sheath 128 includes a tubular member having an axially extending bore in which is slidably received the inner tubular member 132 of the introducer feeder 126.

The split free end of the introducer feeder 126 is preferably formed from either an elastically deformable material or a material having shape memory properties. Formed from such material, the first and second portions 134, 136 of the split free end are provided with a resilient tendency to separate transversely from each other in a spaced apart condition exposing a suburethral implant 2 which is positioned interiorly between the first and second portions 134, 136.

Preferably, the distal end 74 of the suburethral implant introducer assembly 52, and in particular the introducer feeder thereof, is formed with a tissue piercing tip 138 in order to pierce the vaginal canal wall and penetrate tissue in proximity to the patient's urethra. The distal end 74 of the suburethral implant introducer assembly 52, and in particular the introducer feeder 126 thereof, is further preferably formed with a tip 138 shaped to removably seat at least a portion of the suburethral implant 2. More particularly, the tip 138 of the distal end 74 of the introducer assembly 52, and in particular the introducer feeder 126 thereof, has formed in an edge thereof diametrically opposed recesses 140. Each recess 140 receives the hooked end 32 or barb 34 of one of the arms 6 of the suburethral implant, such as the implants 2 shown in FIGS. 1-3 of the drawings. Since the hooked ends 32 or the barbs 24 extend outwardly slightly beyond the diameter of the introducer assembly 52, or more particularly, the diameter of the introducer feeder 126, the hooked ends or barbs of the suburethral implant will engage the tissue on opposite sides of the patient's urethra so that the implant 2 is pulled from the introducer feeder 126 and remains affixed to the surrounding tissue of the urethra when the introducer assembly is retracted from the implant deployment site.

The preferred mechanism of the device of the present invention which extends and retracts the suburethral implant introducer assembly 52 will now be described in greater detail. The mechanism is preferably situated in the housing cavity and is operatively linked to the trigger arm 60 and the introducer assembly 52 and causes the suburethral implant introducer assembly to extend and retract with respect to the vaginal probe 48 in response to pivotal movement of the trigger arm 60 with respect to the housing 54.

Preferably, the mechanism includes a curved toothed rack member 142 which reciprocatingly slides in a conformingly curved guide channel 144 situated within the housing cavity and defined by a pair of spaced apart internal housing walls 146, 148, the diameter of the toothed rack member 142 and the diameter of the guide channel 144 being substantially the same so that the toothed rack member is slidable therein without binding.

The mechanism further includes a pinion gear assembly 150. The pinion gear assembly 150 is operatively linked to the trigger arm 60 and rotates in response to pivotal movement of the trigger arm. The toothed rack member 142 engages the pinion gear assembly 150 and reciprocatingly slides within the guide channel 144 in response to rotation of the pinion gear assembly. The introducer assembly 52 is operatively linked to the toothed rack member 142 and extends and retracts with respect to the vaginal probe 48 in response to reciprocatingly slidable movement of the toothed rack member 142 within the guide channel 144.

The pinion gear assembly 150 preferably includes a first pinion gear 152 and a second pinion gear 154. The second pinion gear 154 is co-axially disposed and fixedly mounted to the first pinion gear 152 so that the first and second pinion gears rotate together. Each of the first and second pinion gears 152, 154 have a toothed outer diameter. The toothed outer diameter of the first pinion gear 152 is greater than the toothed outer diameter of the second pinion gear 154. The trigger arm 60 includes a toothed outer surface 156, preferably formed along an arc of relatively large diameter. The toothed outer surface 156 of the trigger arm 60 engages the second pinion gear 154, with the first pinion gear 152 engaging the toothed rack member 142. One end of a compression spring 158 is affixed to a leg 160 outwardly radially extending from a hub 162 forming part of the trigger arm and from which the finger grip portion 64 of the trigger arm extends. The hub 162 has a central bore 164 formed through the thickness thereof for receiving a pivot pin or tubular member 166 affixed to the housing 54 so that the trigger arm may be pivotally mounted at the hub 162 to the housing. The other end of the compression spring 158 is affixed to a protuberance 168 internally situated within the handle 62 of the housing. The compression spring 158 biases the trigger arm 60 pivotally outwardly from the handle 62.

A surgeon would grasp the device by the handle 62, with his fingers about the finger grip portion 64 of the trigger arm. He would squeeze the trigger arm 60 toward the handle against the force of the compression spring 158. The toothed outer surface 156 of the trigger arm 60 engages the second pinion gear 154 to rotate the gear as the trigger arm is squeezed. The rotation of the second pinion gear 154 causes, in turn, the larger diameter first pinion gear 152 to rotate. The first pinion gear 152 which engages the toothed rack member 142, causes the toothed rack member to slide reciprocatingly in the curved guide channel 144.

The mechanism for extending and retracting the suburethral implant introducer assembly 52 further includes an introducer sheath mounting member 170, an introducer feeder mounting member 172 and a linkage 174 that is preferably fixedly secured to the introducer sheath mounting member 170 and selectively releasably secured to the introducer feeder mounting member 172. More specifically, the introducer sheath mounting member 170 may be in the form of a block which is reciprocatingly slidable within the guide channel 144 in response to movement of the toothed rack member 142. It is preferably fixedly secured to the introducer sheath 128. The proximal end of the sheath 128 may include a radially outwardly extending flange 176, and the mounting member 170 may include an axial bore 178 formed through the thickness thereof which at least partially receives the introducer sheath 128. The mounting block 170 may include a circular recess formed in the inside surface defining the axial bore 178, which recess receives the flange 176 of the introducer sheath 128 so that the mounting member holds the introducer sheath captive within the axial bore 178 formed in the block 170 and so that the sheath 128 and mounting member 170 move reciprocatingly within the guide channel 144 as one.

Similarly, the introducer feeder mounting member 172 may be formed as a block that reciprocatingly slides within the guide channel 144 in response to movement of the toothed rack member 142 therein. The mounting member 172 is fixedly secured to the introducer feeder 126 and, for this purpose, may include a bore 180 formed axially therethrough, with a circular recess formed in the inside wall of the block that defines the axial bore 180, in a manner and with structure similar to that of the introducer sheath mounting member 170. The introducer feeder 126 includes a proximal end which preferably is formed with a radially outwardly extending flange 182. The introducer feeder 126 is received by the axial bore 180 of the introducer feeder mounting member 172, with the flange 182 being received by the recess formed therein, so as to captively hold the introducer feeder 126 to its respective mounting member 172 and so that the introducer feeder and the introducer feeder mounting member reciprocatingly slide within the guide channel 144 as one.

The introducer feeder mounting member 172 is mounted or joined to, or is integrally formed with, the toothed rack member 142 so that movement of the toothed rack member within the guide channel 144 will correspondingly cause movement of the introducer feeder mounting member 172 and the introducer feeder 126 held thereby.

A stop member 184, which could be defined by an internal wall of the housing 54 that extends into the guide channel 144 at an end of the guide channel situated in the vaginal probe 48 and near the introducer assembly exit port 70 formed therein, is provided to selectively stop movement of the introducer sheath mounting member 170, and the introducer sheath 128 held thereby, when the introducer sheath mounting member contacts the stop member 184. The introducer feeder mounting member 172 is spaced in the guide channel 144 apart from the introducer sheath mounting member 170 a predetermined distance and is selectively operatively linked to the introducer sheath mounting member by the linkage 174 so that the introducer sheath 128 and the introducer feeder 126 move together in response to movement of the toothed rack member 142 in the guide channel 144 when the introducer sheath mounting member 170 is not in contact with the stop member 184. However, the introducer feeder 126 moves independently of the introducer sheath 128 in response to movement of the toothed rack member 142 in the guide channel 144 when the introducer sheath mounting member 170 is in contact with and prevented from further movement in at least one direction by the stop member 184.

Even more specifically, the linkage 174 which selectively joins the introducer sheath mounting member 170 to the introducer feeder mounting member 172 includes a proximate end 186 affixed to the introducer sheath mounting member 170 and a resilient distal end 188 situated opposite to the proximate end 186. The linkage 174 further includes a protrusion 190 situated on the distal end 188 thereof. The introducer feeder mounting member 172 further includes a recess 192 formed in a surface thereof. The protrusion 190 is selectively received by the recess 192 so that the introducer sheath mounting member 170 is selectively operatively linked to the introducer feeder mounting member 172. As shown in the drawings, the linkage 174 is preferably formed as a pair of upper and lower leaf spring members 194, 196 which are respectively joined to opposite sides of the introducer sheath mounting member 170 and which sandwich the introducer feeder mounting member between them. Each leaf spring member 194, 196 includes an integrally formed V-shaped protrusion 190 which is respectively releasably received by a complementary shaped recess 192 formed in each opposite side of the mounting member 172.

When the surgeon pulls on the trigger arm 60, the trigger arm turns the pinion gear assembly 150 which, in turn, moves the toothed rack member 142 within the guide channel 144. The toothed rack member 142 engages the introducer feeder mounting member 172, which is linked to the introducer sheath mounting member 170. The two mounting members 170, 172 move as one and, accordingly, so does the introducer feeder 126 and the introducer sheath 128. The introducer sheath 128 is covering the distal end 130 of the introducer feeder 126 and holding the split portions 134, 136 of the distal end of the introducer feeder 126 together, with the suburethral implant 2 in its folded state situated between and held captive by the two split end portions. This stage of extending the suburethral implant introducer assembly 52 is shown in FIG. 14 of the drawings.

Figure 15:
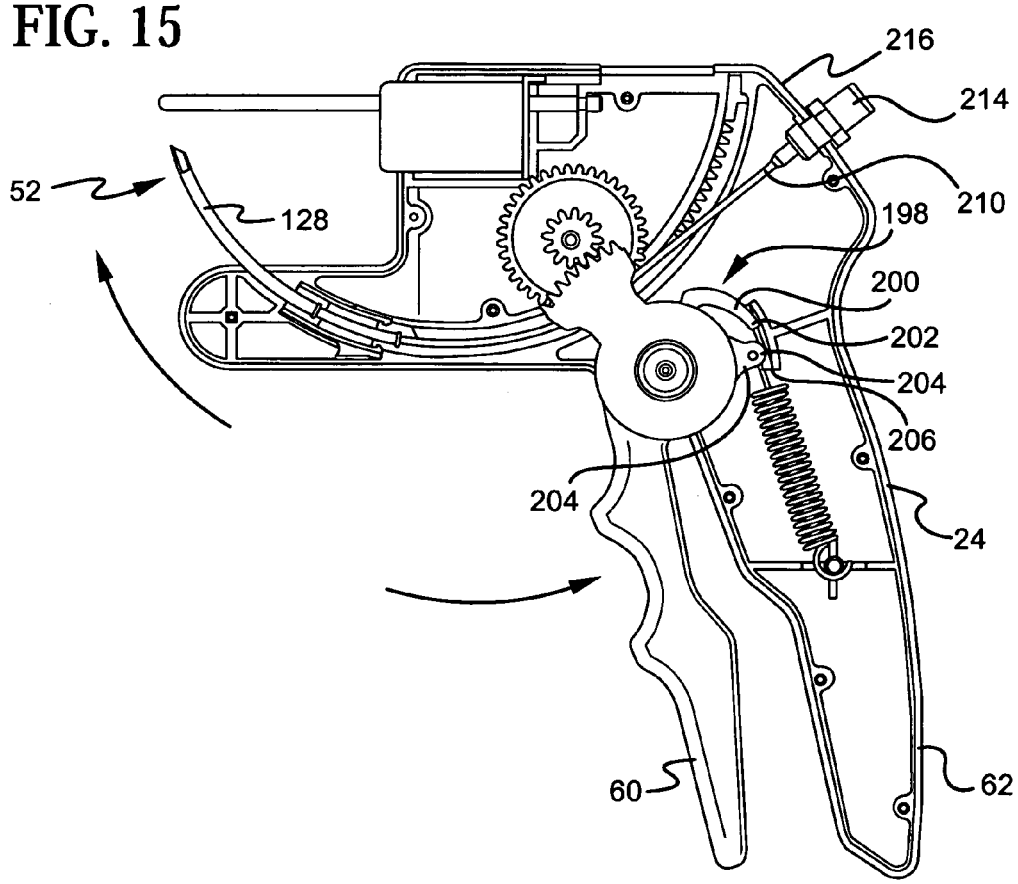
FIG. 15 is a cross-sectional view of the device of the present invention shown in FIGS. 4 and 5 and illustrating the operation of the device in deploying an implant for treating SUI.
Figure 16:
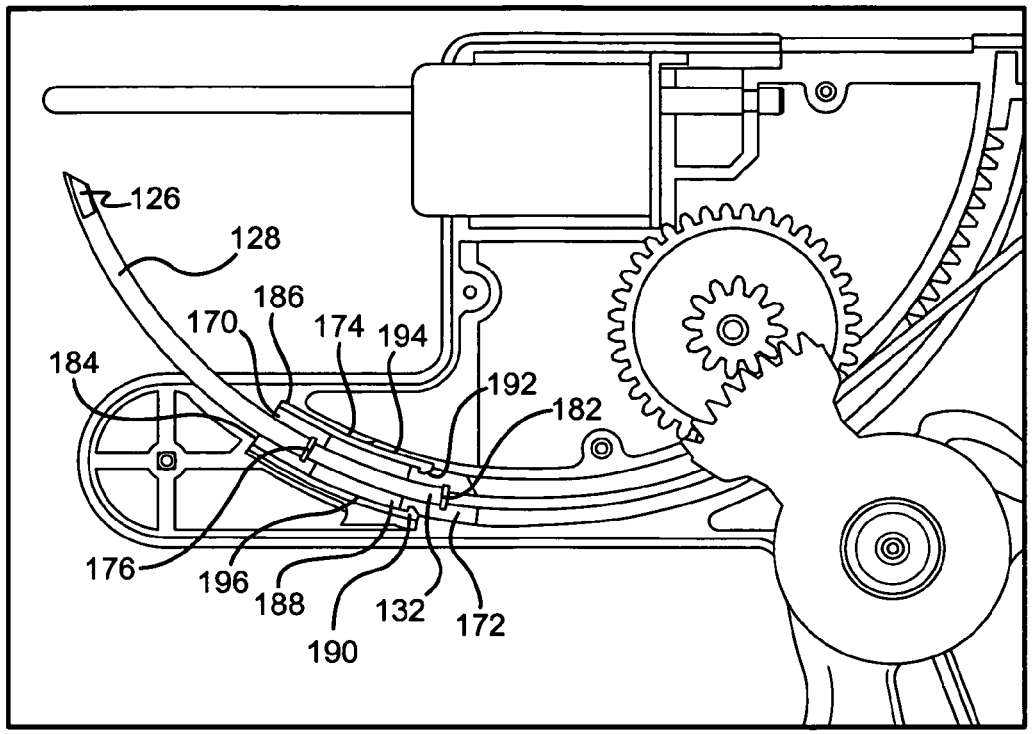
FIG. 16 is an enlarged cross-sectional view of the device of the present invention shown in FIGS. 4 and 5 and illustrating the operation of the device in deploying an implant for treating SUI.

With further pivotal movement of the trigger arm 60, as shown in FIG. 15 of the drawings, the introducer sheath mounting member 170 and introducer feeder mounting member 172 move in the guide channel 144 with the toothed rack member 142 towards the distal end of the guide channel, forcing both the introducer sheath 128 and the introducer feeder 126 covered by the introducer sheath outwardly through the exit port 70 and towards the urethra locator probe 50. The introducer assembly 52 stops just beneath a portion of the urethra which is held in position by the urethra locator probe 50, as shown in FIG. 16.

Figure 17:
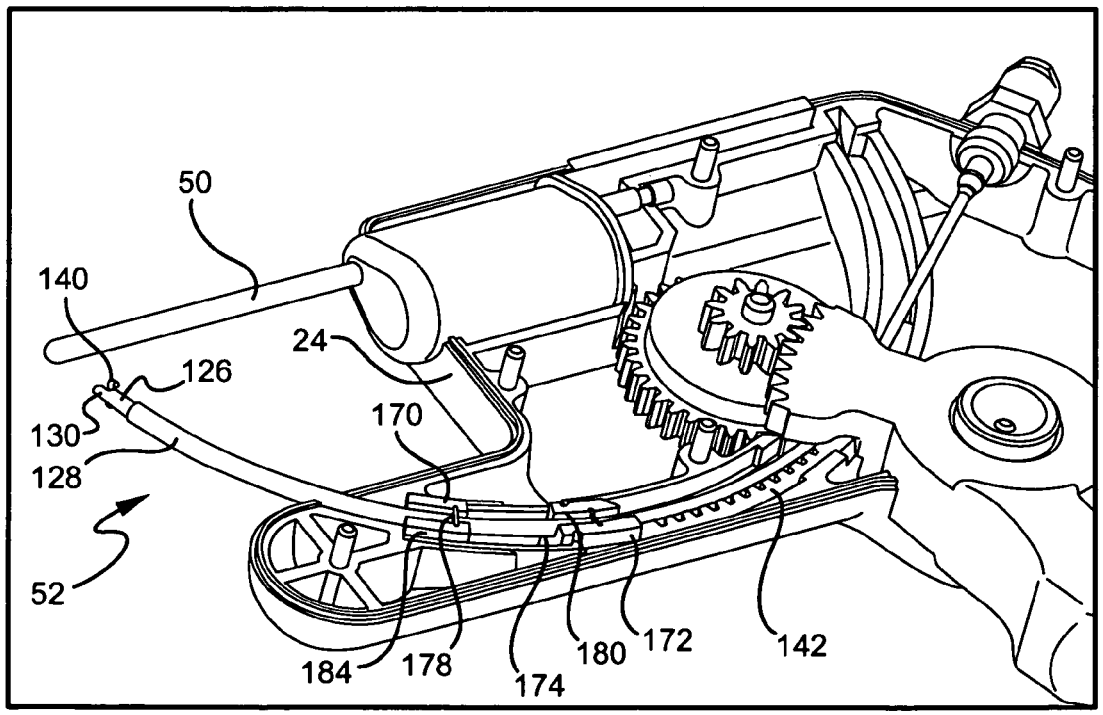
FIG. 17 is a front perspective view of a portion of the device of the present invention shown in FIGS. 4 and 5 and illustrating the operation of the device in deploying an implant for treating SUI.
Figure 18:
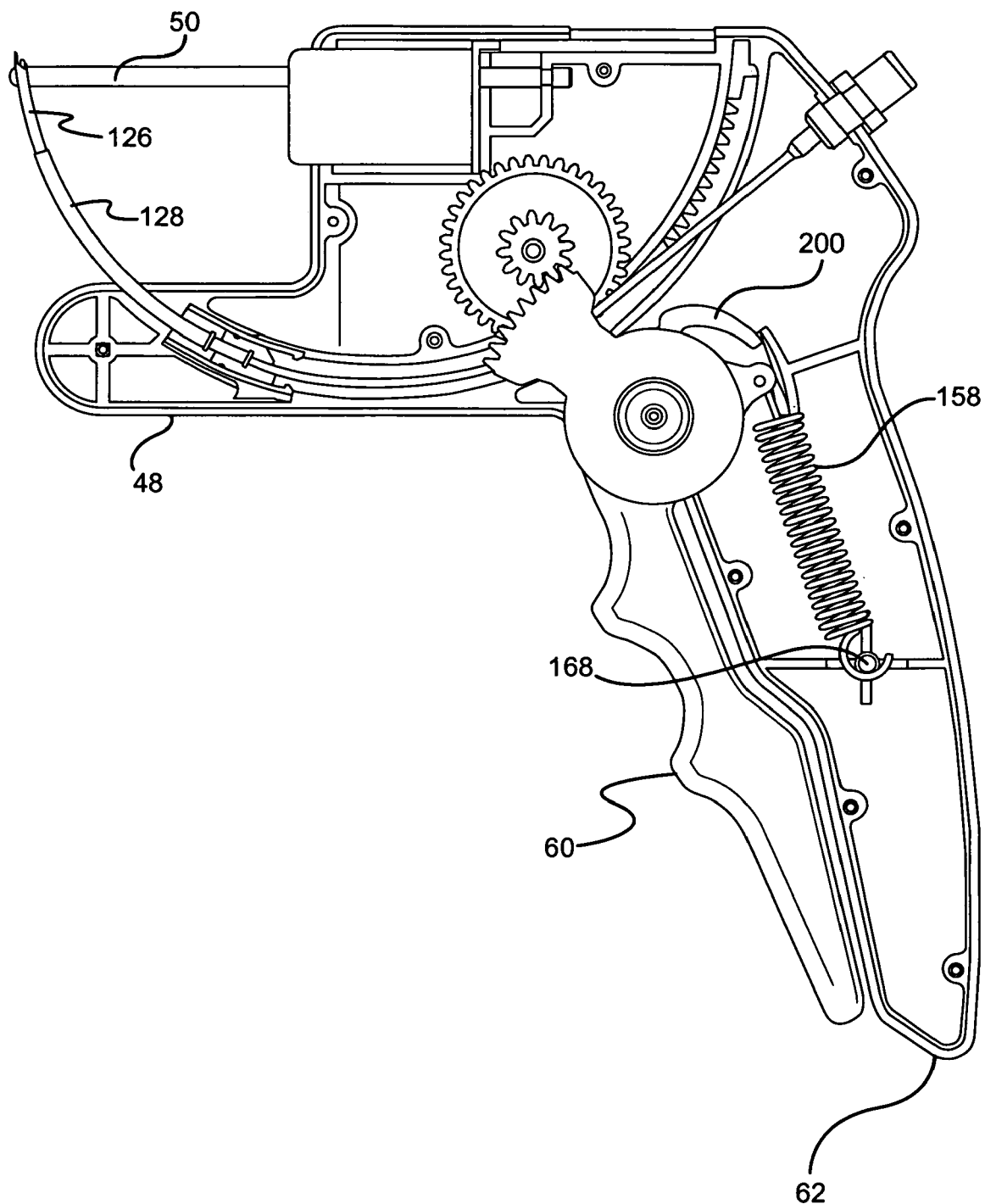
FIG. 18 is a cross-sectional view of the device of the present invention shown in FIGS. 4 and 5 and illustrating the operation of the device in deploying an implant for treating SUI.
Figure 19:
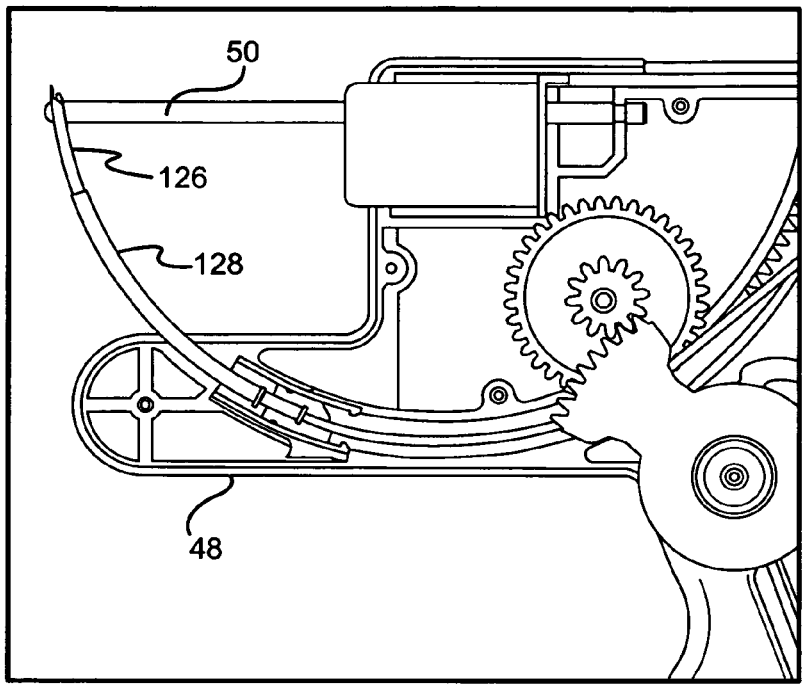
FIG. 19 is a side view of a portion of the device of the present invention shown in FIGS. 4 and 5 and illustrating the operation of the device in deploying an implant for treating SUI.
Figure 20:
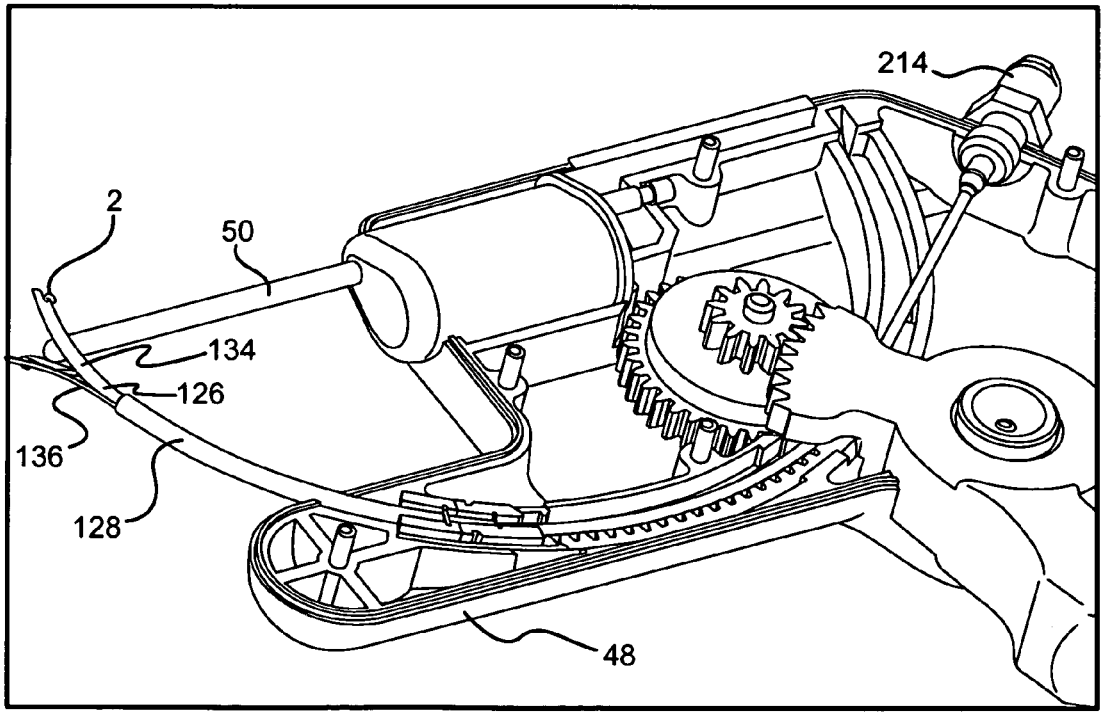
FIG. 20 is a front perspective view of a portion of the device of the present invention shown in FIGS. 4 and 5 and illustrating the operation of the device in deploying an implant for treating SUI.
Figure 21:
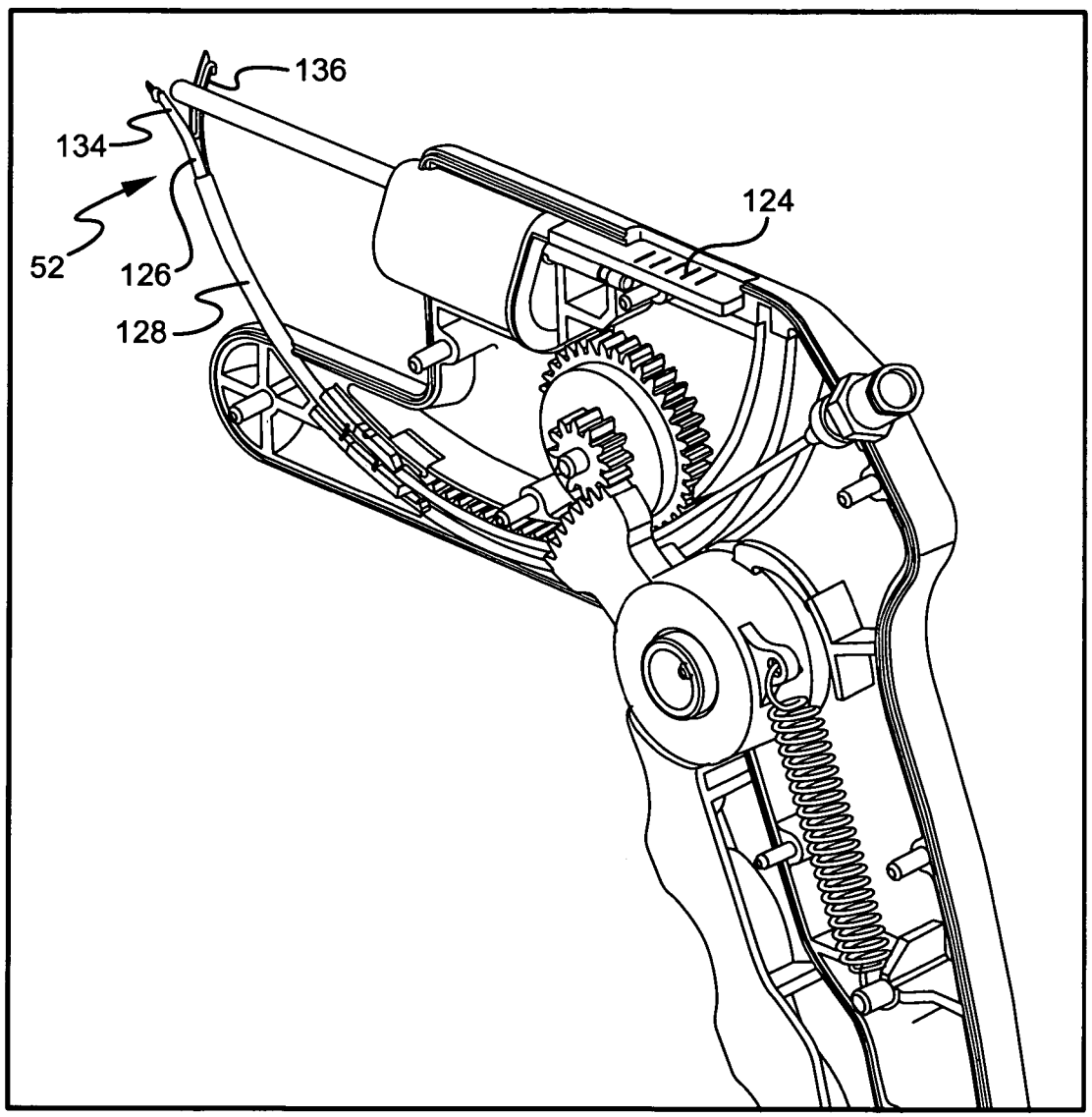
FIG. 21 is a rear perspective view of a portion of the device of the present invention shown in FIGS. 4 and 5 and illustrating the operation of the device in deploying an implant for treating SUI.
Figure 22:
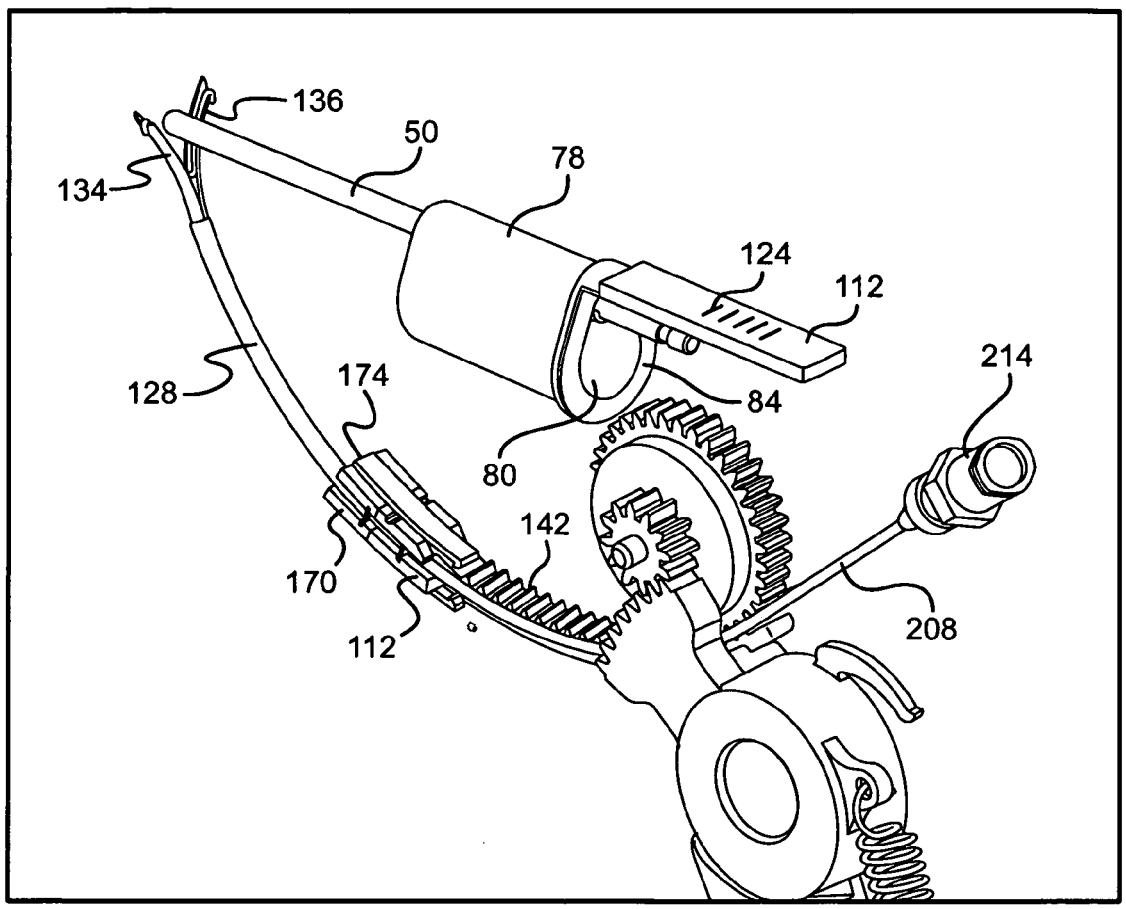
FIG. 22 is a rear perspective view of certain components of the device of the present invention shown in FIGS. 4 and 5 and illustrating the operation of the device in deploying an implant for treating SUI.

Further pivotal movement of the trigger arm 60 causes the toothed rack member 142 to force the introducer sheath mounting member 170 against the stop member 184 to prevent further movement of the introducer sheath mounting member 170 and the introducer sheath 128 held thereby, as shown by FIG. 17 of the drawings. Now, continuing to pull the trigger arm 60 back towards the handle 62 causes the introducer feeder mounting member 172 to decouple from the introducer sheath mounting member 170, as the introducer sheath mounting member is prevented from further movement in the guide channel 144 by the stop member 184. The protrusions 190 situated on the distal end of the linkage leaf spring members 194, 196 are forced out of the recesses 192 formed in the introducer feeder mounting member 172 to unlink the two mounting members 170, 172 and to permit further movement of the introducer feeder mounting member 172 within the guide channel 144 in response to further movement of the toothed rack member 142, as shown in FIG. 18 of the drawings. This further movement of the introducer feeder mounting member 172 causes the split distal end 130 of the introducer feeder 126 to move axially beyond the end of the covering introducer sheath 128 to expose the split end portions 134, 136 of the introducer feeder. As shown by FIGS. 19-22 of the drawings, the first and second portions 134, 136 of the split free end of the introducer feeder 126 separate transversely from each other and fork around the urethra which, although not shown in the drawings, is held in place by the urethra locator probe 50. The implant 2, which was protectively housed by and between the first and second portions 134, 136 of the split free end of the introducer feeder 126, now opens and unfolds, as its arms 6 with their hooked ends 32 or barbs 34 are carried and spread by the separating first and second portions 134, 136 of the split free end of the introducer feeder 126, so that the arms 6 pass on diametrically opposite sides of the urethra held in position by the urethra locator probe 50. The split ends of the introducer feeder 126 preferably bypass the urethra probe 50, as shown by FIGS. 19-22, which of course also holds the urethra in position. The hooked ends 32 or barbs 34 of the suburethral implant 2, which are seated at the tips of the first and second portions 134, 136 of the split free end of the introducer feeder 126 engage tissue on opposite sides of the urethra and become affixed thereto.

When the surgeon releases the trigger arm 60 at the end of the full stroke of pivoting movement of the trigger arm, the compression spring 158 attached thereto causes the trigger arm 60 to pivot outwardly away from the handle 62. The toothed outer surface 156 of the trigger arm causes the pinion gear assembly 150 to rotate in an opposite direction from that when the trigger arm was squeezed which, in turn, forces the toothed rack member 142 to slide within the guide channel 144 towards the proximal end thereof, i.e., away from the vaginal probe 48. The toothed rack member 142 pulls the introducer feeder mounting member 172 backwardly in the guide channel 144 which correspondingly retracts the introducer feeder 126 into the introducer sheath 128, which sheath forces the split ends 134, 136 of the introducer feeder to close. Further release of the trigger arm 60 causes more movement of the introducer feeder mounting member 172 within the guide channel 144 to where the introducer feeder mounting member and the introducer sheath mounting member 170 are separated by the same earlier predetermined distance such that the protrusions 190 on the distal ends of the linkage leaf spring members 194, 196 are aligned with and received by the recesses 192 formed in the introducer feeder mounting member 172, causing the two mounting members 170, 172 to again be linked together. Further release of the trigger arm 60 retracts the introducer feeder 126 and the introducer sheath 128 together into the exit port 70 formed in the vaginal probe 48.

The suburethral implant 2, which had its two arms 6 seated in the recesses 140 formed in the tips of the split first and second end portions 134, 136 of the introducer feeder 126, is dislodged from the split end portions due to its engagement with the tissue surrounding the patient's urethra and is held in place thereby, straddling the urethra, with the main body portion 4 thereof supporting the urethra at a desired location along the length of the urethra.

To prevent incomplete deployment of the suburethral implant, the device of the present invention preferably includes an anti-backup mechanism 198 operatively linked to the trigger arm 60. More specifically, and as shown in FIG. 18 of the drawings, the anti-backup mechanism 198 preferably includes a cantilevered resilient leg 200 extending outwardly from the hub 162 of the trigger arm, the leg 200 having a free end on which is situated a toothed pawl 202. A ratchet assembly which includes a toothed ratchet 204 is situated within the housing cavity in proximity to the hub 162 of the trigger arm 60 and engageable by the pawl 202 of the cantilevered leg 200. When the trigger arm 60 is squeezed by the surgeon, the toothed pawl 202 slips over the toothed ratchet 204 to allow such pivotal movement of the trigger arm in one direction only, the engagement of the pawl 202 and the toothed ratchet 204 preventing movement of the trigger arm in an opposite direction at least until the trigger arm 60 has been moved to its full extent required for deployment of the suburethral implant 2. At this point, the toothed pawl 202 reaches the end of the toothed ratchet 204 and, due to its resiliency also in an axial direction, springs out of engagement with the toothed ratchet 204 and engages a smooth, untoothed surface 206 of the ratchet assembly situated and extending along the side of the toothed ratchet 204 to allow the trigger arm 60 to pivot in an opposite direction away from the handle 62 under the force of the compression spring 158, causing the suburethral implant introducer assembly 52 to be fully retracted through the exit port 70 formed in the vaginal probe 48. The surgeon may now withdraw the vaginal probe 48 and urethra locator probe 50 from the patient's vaginal canal and urethra without injury to the patient, as the introducer assembly 52 is fully retracted within the interior of the vaginal probe.

Another feature of the device of the present invention for deploying a suburethral implant is its ability to direct anesthesia at the site where the introducer assembly 52 pierces the vaginal canal wall. For this purpose, the device preferably includes a fluid conduit 208. The fluid conduit 208 has an axial bore extending longitudinally therethrough, and a first open axial end 210 and a second open axial end 212 which is situated opposite the first open axial end 210, the first and second open axial ends 210, 212 being in fluid communication with the axial bore. A Luer fitting 214 is mounted to a rear wall 216 of the housing 54 through an opening formed through the thickness thereof. The second end 212 of the fluid conduit 208 is coupled to the Luer fitting 214, and the first end 210 of the conduit is co-extensively situated at the introducer assembly exit port 70. Thus, the fluid conduit 208 extends between the housing 54, preferably through the tubular inner introducer feeder 126 and tubular outer introducer sheath 128 and through the bores 178, 180 formed through the introducer sheath mounting member 170 and introducer feeder mounting member 172, and ends directly at the introducer assembly exit port 70. The fluid conduit 208 preferably does not move as the introducer assembly 52 is extended and retracted through the exit port 70, as the introducer feeder 126 moves reciprocatingly on the fluid conduit 208. The surgeon may connect the Luer fitting 214 to an appropriate source of anesthesia in order to supply anesthesia through the fluid conduit 208 directly to the exit port 70 formed in the vaginal probe 48 which is where the introducer assembly 52 will pierce the wall of the vaginal canal. Alternatively, the fluid conduit 208 may extend from the Luer fitting 214 to a fluid output port (not shown) formed through the thickness of the wall of the vaginal probe 48 preferably in close proximity to the introducer assembly exit port 70 in order to provide anesthesia close to the site where the introducer assembly 52 will pierce the vaginal canal wall.

With the suburethral implant 2 and the device 46 for deploying the suburethral implant, both of which are formed in accordance with the present invention, the implant 2 may be deployed in a minimally invasive manner at a precise location to support the patient's urethra. To deploy the suburethral implant at the desired location in the patient's body, the vaginal probe 48 is inserted into the patient's vaginal canal, with the urethra locator probe 50 simultaneously inserted into the urethra of the patient. The suburethral implant introducer assembly 52 is extended through the introducer assembly exit port 70 formed in the vaginal probe 48. Prior to or while the suburethral implant introducer assembly 52 is being extended from the exit port 70, anesthesia is ejected through the exit port to the site where the introducer assembly will pierce the wall of the vaginal canal.

The introducer sheath 128 and the introducer feeder 126 of the introducer assembly 52 are simultaneously extended outwardly from the exit port 70. At a certain point in the deployment of the suburethral implant 2, the inner introducer feeder 126 is extended farther from the exit port 70, without the introducer sheath 128, so that the distal end portion 130 of the inner introducer feeder 126 is uncovered by the introducer sheath 128 as the introducer assembly is extended further from the exit port. The suburethral implant 2, which is removably mounted on the distal end 74 of the introducer assembly 52, is then deployed at a location in proximity to the patient's urethra held in place by the urethra locator probe 50. The introducer assembly 52 is then retracted through the exit port 70 formed in the vaginal probe 48.

To prevent over-insertion of either or both of the urethra locator probe 50 and the vaginal probe 48 into respectively the patient's urethra and vaginal canal, the insertion depth stop 76 is used to contact with a patient's body near the urethra orifice. Also, to determine the relative depth of insertion of either or both of the urethra locator probe 50 and the vaginal probe 48 into the patient's urethra and vaginal canal, the surgeon may refer to the insertion depth indicator 110 of the device, which is operatively linked to the insertion depth stop 76.

Accordingly, the device of the present invention allows the surgeon to secure a portion of the patient's vaginal canal in a first position, and to secure a portion of the patient's urethra in a second position relative to the first position of the portion of the patient's vaginal canal. Then, the surgeon can extend the introducer assembly 52 through the patient's vaginal canal at the portion thereof which is held in the desired first position toward the portion of the patient's urethra which is held in the desired second position. The suburethral implant 2, which is removably mounted on the distal end 74 of the introducer assembly 52, may then be deployed at a location in proximity to the patient's urethra, which is held in place by the urethra locator probe 50, and in alignment with the direction of movement of the introducer assembly 52. Then, the suburethral implant introducer assembly 52 may be retracted from the patient's vaginal canal and back into the vaginal probe 48 of the device so that it does not protrude therefrom to allow the vaginal probe 48 and urethra locator probe 50 to be removed without causing injury to the patient's tissue.

As is evident from the foregoing description, the suburethral implant of the present invention requires no incisions in the abdominal wall and no needles for its surgical placement in the patient. A minimally invasive procedure is all that is required to treat patients suffering from stress urinary incontinence (SUI). The device of the present invention for deploying the suburethral implant facilitates and shortens the surgical procedure for deploying the implant in the patient. Since the surgical procedure is less invasive than other surgical procedures for treating SUI, less anesthesia is required to deploy the implant.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A suburethral implant for treating stress urinary incontinence, which comprises:
    a main body for supporting a patient's urethra, the main body having a length defining a longitudinal axis, wherein the main body is straight along the longitudinal axis, the main body having opposite lateral side portions; and the main body having a transverse axis extending between the opposite lateral side portions thereof, the transverse axis being perpendicular to the longitudinal axis of the main body, and wherein the main body is concave along the transverse-axis;
    a pair of spaced apart resilient arms extending from the main body, each arm having a tissue engaging portion, wherein the implant has an undeployed state in which the arms are folded over the main body and extend along the length and the longitudinal axis of the main body and a deployed state in which the arms are unfolded and extend in a transverse direction to the longitudinal axis of the main body.

2. A suburethral implant for treating stress urinary incontinence as defined by claim 1, wherein the main body includes a plurality of openings formed through the thickness thereof.

3. A suburethral implant for treating stress urinary incontinence as defined by claim 2, wherein the main body is at least partially formed from a mesh material.

4. A suburethral implant for treating stress urinary incontinence as defined by claim 1, wherein the tissue engaging portion of each arm includes a barb to facilitate securing the suburethral implant to tissue in proximity to the patient's urethra.

5. A suburethral implant for treating stress urinary incontinence as defined by claim 1, wherein the tissue engaging portion of each arm includes a hook to facilitate securing the suburethral implant to tissue in proximity to the patient's urethra.

6. A suburethral implant for treating stress urinary incontinence as defined by claim 1, wherein at least each arm is formed from one of a resilient, elastically deformable material and a material having shape memory properties.

7. A suburethral implant for treating stress urinary incontinence as defined by claim 6, wherein the arms overlie a top surface of the main body when the suburethral implant is in the folded, undeployed state.

8. A suburethral implant for treating stress urinary incontinence as defined by claim 6, wherein each arm includes a spring portion.

9. A suburethral implant for treating stress urinary incontinence as defined by claim 8, wherein the spring portion of each arm includes a curved portion defining an open pocket.

10. A suburethral implant for treating stress urinary incontinence as defined by claim 9, wherein each arm extends from a respective lateral side portion of the main body; wherein each arm includes a first side and a second side opposite the first side; and wherein the main body includes a first portion extending outwardly from the first side of the arms in a first direction along the longitudinal axis of the main body, and a second portion extending outwardly from the second side of the arms in a second direction along the longitudinal axis of the main body which is opposite to the first direction, the suburethral implant being foldable in the undeployed state, wherein the second portion is at least partially received by the open pockets defined by the curved portions of the arms such that the arms and second portion of the main body extend generally in the second direction along the longitudinal axis of the main body, the suburethral implant being unfoldable in the deployed state, wherein the second portion of the main body is not received by the open pockets defined by the curved portions of the arms such that the arms extend in a transverse direction to the longitudinal axis in which the first and second portions of the main body extend.

11. A suburethral implant for treating stress urinary incontinence as defined by claim 1, wherein the length of the main body is between about 0.5 mm and about 10 mm.

12. A suburethral implant for treating stress urinary incontinence as defined by claim 11, wherein the length of the main body is about 3 mm.

13. A suburethral implant for treating stress urinary incontinence as defined by claim 11, wherein the length of the main body is about 2 mm.

14. A suburethral implant for treating stress urinary incontinence as defined by claim 1, wherein the spaced apart arms have proximal ends integrally formed with the main body.

15. A suburethral implant for treating stress urinary incontinence as defined by claim 1, wherein the spaced apart arms have a length of about 1-10 mm.

16. A suburethral implant for treating stress urinary incontinence as defined by claim 1, wherein the spaced apart arms have a length of about 2 mm.

17. A suburethral implant for treating stress urinary incontinence as defined by claim 1, wherein proximal ends of the spaced apart arms are permanently fixed to the main body.

18. A suburethral implant for treating stress urinary incontinence as defined by claim 1, wherein the spaced apart arms meet the main body when in the folded, undeployed, state.

19. A suburethral implant for treating stress urinary incontinence as defined by claim 1, wherein each of the arms includes a spring portion for normally urging the arms to extend into the unfolded, deployed state.

20. A suburethral implant for treating stress urinary incontinence as defined by claim 1, wherein each of the spaced apart arms has a distal end having a hook or a barb integrally formed thereon.

21. A suburethral implant for treating stress urinary incontinence as defined by claim 1, wherein the main body, the pair of spaced apart arms and the tissue engaging portions of the pair of spaced apart arms comprise a single piece of material.

22. A suburethral implant for treating stress urinary incontinence, which comprises:
    a main body for supporting a patient's urethra, the main body including a V-shaped member generally residing in and extending along a longitudinal plane and having a pair of legs with proximal ends connected together at a flexible apex joint and distal free ends opposite the proximal ends; and
    a pair of spaced apart arms extending from the V-shaped member, each arm being connected to one of the distal free ends of the legs at flexible joints, each arm having a tissue engaging portion, wherein the suburethral implant has an undeployed state in which the arms and the V-shaped member extend generally along the longitudinal plane of the V-shaped member, and a deployed state in which the arms extend in a transverse direction to the longitudinal plane in which the V-shaped member generally resides.

23. A suburethral implant for treating stress urinary incontinence as defined by claim 22, wherein the V-shaped member and each arm are integrally formed from a single, selectively shaped, rod-like member.

24. A suburethral implant for treating stress urinary incontinence as defined by claim 23, wherein the rod-like member is formed from a Nitinol wire.

25. A suburethral implant for treating stress urinary incontinence as defined by claim 22, wherein the V-shaped member includes the pair of legs, and the flexible apex joint joining the legs together.

26. A suburethral implant for treating stress urinary incontinence as defined by claim 25, wherein each flexible arm joint is situated on a respective leg of the V-shaped member and interconnects a respective leg of the V-shaped member with one of the arms of the pair of spaced apart arms.

27. A suburethral implant for treating stress urinary incontinence as defined by claim 22, wherein at least one of the V-shaped member and each arm is formed from one of a resilient, elastically deformable material and a material having shape memory properties.

28. A suburethral implant for treating stress urinary incontinence as defined by claim 22, wherein the tissue engaging portion of each arm includes a barb to facilitate securing the suburethral implant to tissue in proximity to the patient's urethra.

29. A suburethral implant for treating stress urinary incontinence as defined by claim 22, wherein the tissue engaging portion of each arm includes a hook to facilitate securing the suburethral implant to tissue in proximity to the patient's urethra.

30. A suburethral implant for treating stress urinary incontinence as defined by claim 22, wherein the V-shaped member defines a longitudinal plane, and wherein the suburethral implant is foldable to an undeployed state in which the pair of legs of the V-shaped member and the pair of spaced arms extend generally along the longitudinal plane defined by the V-shaped member and is unfoldable to a deployed state in which the legs of the V-shaped member are angled outwardly from one another and the arms extend in a transverse direction to the longitudinal plane defined by the V-shaped member.

31. A suburethral implant for treating stress urinary incontinence as defined by claim 22, wherein the flexible apex joint normally urges the legs of the V-shaped member to move away from one another.

32. A suburethral implant for treating stress urinary incontinence as defined by claim 22, wherein the distal ends of the legs are closer together when the suburethral implant is in an undeployed state and further apart when the suburethral implant is in a deployed state.

33. A suburethral implant for treating stress urinary incontinence as defined by claim 22, wherein the pair of spaced apart arms have distal ends that are further from the flexible apex joint when the suburethral implant is in an undeployed state and closer to the flexible apex joint when the suburethral implant is in a deployed state.

34. A suburethral implant for treating stress urinary incontinence as defined by claim 22, wherein each of the spaced apart arms has a length of between about 1-10 mm.

35. A suburethral implant for treating stress urinary incontinence as defined by claim 22, wherein each of the spaced apart arms has a length of about 2 mm.

36. A suburethral implant for treating stress urinary incontinence, which comprises:
a main body for supporting a patient's urethra, the main body having a length defining a longitudinal axis of the main body, wherein the main body is straight along the longitudinal axis thereof and further wherein the main body has a transverse axis extending between opposite lateral side portions of the main body, the transverse axis being perpendicular to the longitudinal axis of the main body, and wherein the main body is concave along the transverse-axis;
a pair of spaced apart resilient arms extending from the main body, each arm having a tissue engaging portion, wherein the implant has an undeployed state in which the arms are folded over the main body and extend along the length and the longitudinal axis of the main body and a deployed state in which the arms are unfolded and extend in a transverse direction to the longitudinal axis of the main body.

37. A suburethral implant for treating stress urinary incontinence as defined by claim 36, wherein the tissue engaging portion of each arm includes a barb to facilitate securing the suburethral implant to tissue in proximity to the patient's urethra.

38. A suburethral implant for treating stress urinary incontinence as defined by claim 36, wherein the tissue engaging portion of each arm includes a hook to facilitate securing the suburethral implant to tissue in proximity to the patient's urethra.

39. A suburethral implant for treating stress urinary incontinence as defined by claim 36, wherein at least one of the main body and the pair of arms is formed from one of a resilient, elastically deformable material and a material having shape memory properties.

40. A suburethral implant for treating stress urinary incontinence as defined by claim 39, wherein each of the arms includes a spring portion for urging the arms from the folded, undeployed state to the unfolded, deployed state.

41. A suburethral implant for treating stress urinary incontinence as defined by claim 36, wherein the pair of spaced apart arms have proximal ends permanently connected with the main body.

42. A suburethral implant for treating stress urinary incontinence as defined by claim 36, wherein the pair of spaced apart arms have a length of about 1-10 mm.

43. A suburethral implant for treating stress urinary incontinence as defined by claim 36, wherein the pair of spaced apart arms have a length of about 2 mm.

44. A suburethral implant for treating stress urinary incontinence as defined by claim 36, wherein the spaced apart arms meet the main body when in the folded, undeployed, state.

45. A suburethral implant for treating stress urinary incontinence as defined by claim 36, wherein each of the spaced apart arms includes a spring portion for normally urging the arms to spring from the folded, undeployed state to the unfolded, deployed state.

46. A suburethral implant for treating stress urinary incontinence as defined by claim 36, wherein each of the spaced apart arms has a distal end having the tissue engaging portion integrally formed thereon.

* * * * *